(12) United States Patent
Wu

(10) Patent No.: US 11,353,417 B2
(45) Date of Patent: Jun. 7, 2022

(54) RISK FACTOR MONITORING

(71) Applicant: ASCENSIA DIABETES CARE HOLDINGS AG, Basel (CH)

(72) Inventor: Huan-Ping Wu, Granger, IN (US)

(73) Assignee: ASCENSIA DIABETES CARE HOLDINGS AG, Basel (CH)

(*) Notice: Subject to any disclaimer, the term of this patent is extended or adjusted under 35 U.S.C. 154(b) by 437 days.

(21) Appl. No.: 16/466,938

(22) PCT Filed: Dec. 1, 2017

(86) PCT No.: PCT/IB2017/057584
§ 371 (c)(1),
(2) Date: Jun. 5, 2019

(87) PCT Pub. No.: WO2018/104835
PCT Pub. Date: Jun. 14, 2018

(65) Prior Publication Data
US 2019/0346399 A1  Nov. 14, 2019

Related U.S. Application Data

(60) Provisional application No. 62/430,232, filed on Dec. 5, 2016.

(51) Int. Cl.
*G08B 21/04* (2006.01)
*G01N 27/327* (2006.01)
(Continued)

(52) U.S. Cl.
CPC ....... *G01N 27/3274* (2013.01); *A61B 5/1473* (2013.01); *A61B 5/14532* (2013.01);
(Continued)

(58) Field of Classification Search
CPC ............ A61B 5/14532; A61B 5/14546; A61B 5/1473; A61B 2562/0238; A61B 5/0059;
(Continued)

(56) References Cited

U.S. PATENT DOCUMENTS 8,002,965 B2  8/2011  Beer
8,026,104 B2  9/2011  Wu
(Continued)

FOREIGN PATENT DOCUMENTS

CN  109690304 A   4/2019
EP  3 021 112 A1  5/2016
(Continued)

OTHER PUBLICATIONS

International Search Report and Written Opinion of the International Searching Authority corresponding to co-pending International Patent Application No. PCT/IB2017/057584 dated Feb. 15, 2018 (13 pages).

(Continued)

*Primary Examiner* — Daniel Previl
(74) *Attorney, Agent, or Firm* — Nixon Peabody LLP

(57) ABSTRACT

Methods, devices, and systems are disclosed for the determination and logging of risk factor parameters associated with a sample, in association with the measurement of a concentration of an analyte in the sample. The methods, devices, and systems provide for applying an input signal to a sample via an electrode. The input signal has at least one excitation. The methods, devices, and systems further provide for measuring an output signal responsive to the input signal. The methods, devices, and systems further provide for determining a concentration of an analyte within the sample based on the output signal, and determining at least one risk factor parameter associated with at least one species in the sample other than the analyte.

36 Claims, 13 Drawing Sheets

(51) Int. Cl.
*A61B 5/145* (2006.01)
*A61B 5/1473* (2006.01)
*A61B 5/00* (2006.01)
*G01N 33/49* (2006.01)

(52) U.S. Cl.
CPC ........ *A61B 5/14546* (2013.01); *A61B 5/7275* (2013.01); *G01N 33/49* (2013.01)

(58) Field of Classification Search
CPC ........ A61B 5/150022; A61B 5/150343; A61B 5/150358; A61B 5/150755; A61B 5/7275; G01N 27/3274; G01N 2800/32; G01N 33/6893; G01N 2333/70596; G01N 2800/042; G01N 2800/323; G01N 2800/50; G01N 2800/52; G01N 2800/56; G01N 33/54386; G01N 33/566; G01N 2030/8822; G01N 21/6428; G01N 30/7233; G01N 33/54313; G01N 33/68; G01N 33/6848; G01N 33/92; G01N 2001/021; G01N 2021/7783; G01N 2021/7786; G01N 21/645; G01N 21/6452; G01N 21/6454; G01N 21/77; G01N 2201/024; G01N 2405/00; G01N 2800/342; G01N 2800/7085; G01N 33/49; G01N 33/491; G01N 33/492; G01N 33/5304; G01N 33/54306; G01N 33/54373; G01N 33/544; G01N 33/552; G01N 33/57434; G01N 33/6887; G01N 33/6896; G01N 35/0098; G01N 35/028; C07K 16/2896; Y02A 50/30; B01J 2219/005; B01J 2219/00725; B01J 19/0046; B01J 2219/00286; B01J 2219/00317; B01J 2219/00353; B01J 2219/00389; B01J 2219/00414; B01J 2219/00416; B01J 2219/00468; B01J 2219/00497; B01J 2219/00576; B01J 2219/00578; B01J 2219/00585; B01J 2219/00605; B01J 2219/0061; B01J 2219/00612; B01J 2219/00626; B01J 2219/00637; B01J 2219/00659; B01J 2219/00677; B01J 2219/00689; B01J 2219/00702; B01J 2219/00707; B01J 2219/00731; C40B 40/06; C40B 40/10; C40B 60/14; C40B 40/12; C40B 50/14; A61P 35/04; B01L 2300/0681; B01L 2300/0819; B01L 2300/0877; B01L 2300/0887; B01L 2400/0487; B01L 3/5023; B01L 3/5025; B01L 3/502707; B01L 3/502715; B01L 3/502738; B01L 3/502761; B82Y 30/00; G16B 20/00; G16B 40/00; G16B 40/10; Y10S 436/807; Y10S 436/809

USPC ........... 340/539.12, 539.13–539.14, 539.24, 340/539.19, 568.1, 571, 572.1–572.9, 588
See application file for complete search history.

(56) References Cited

U.S. PATENT DOCUMENTS

| | | | |
|---|---|---|---|
| 8,147,674 B2 * | 4/2012 | Wu | G01N 27/3273 205/792 |
| 8,404,100 B2 | 3/2013 | Wu | |
| 8,425,757 B2 | 4/2013 | Wu | |
| 8,744,776 B2 * | 6/2014 | Wu | G01N 27/416 702/19 |
| 9,164,076 B2 * | 10/2015 | Huang | G01N 27/3274 |
| 9,222,910 B2 * | 12/2015 | Wu | G01N 27/3274 |
| 9,228,978 B2 * | 1/2016 | Wu | G01N 27/48 |
| 9,958,410 B2 | 5/2018 | Wu | |
| 2008/0280376 A1 * | 11/2008 | Handberg | G01N 33/54386 436/501 |
| 2009/0177406 A1 | 7/2009 | Wu | |
| 2010/0267161 A1 | 10/2010 | Wu | |
| 2011/0231105 A1 | 9/2011 | Wu | |
| 2012/0095318 A1 | 4/2012 | Galley | |
| 2013/0116526 A1 | 5/2013 | Javitt | |
| 2014/0027308 A1 | 1/2014 | Harrison | |
| 2014/0138261 A1 | 5/2014 | Colas | |
| 2017/0046501 A1 * | 2/2017 | Coleman | G16H 20/13 |

FOREIGN PATENT DOCUMENTS

| | | |
|---|---|---|
| WO | WO 2006/110504 A1 | 10/2006 |
| WO | WO 2007/013915 A1 | 2/2007 |
| WO | WO 2007/040913 A1 | 4/2007 |
| WO | WO 2008/051742 A2 | 5/2008 |
| WO | WO 2009/042631 A2 | 4/2009 |
| WO | WO 2009/075951 A1 | 6/2009 |
| WO | WO 2009/108239 A2 | 9/2009 |
| WO | WO 2010/006253 A1 | 1/2010 |
| WO | WO 2010/077660 A1 | 7/2010 |
| WO | WO 2011/119533 A1 | 9/2011 |
| WO | WO 2011/156152 A1 | 12/2011 |
| WO | WO 2011/156325 A2 | 12/2011 |
| WO | WO 2018/011692 A1 | 1/2018 |

OTHER PUBLICATIONS

International Search Report and Written Opinion of the International Searching Authority corresponding to co-pending International Patent Application No. PCT/IB2017/054133 dated Dec. 1, 2017 (18 pages).

Thevenot, D. R. et al., "Electrochemical Biosensors: recommended definitions and classification," Pure and Applied Chemistiy, 71(12): 2333-2348, Jan. 1999.

* cited by examiner

RISK FACTOR MONITORING

CROSS-REFERENCE TO RELATED APPLICATIONS

The present application is a national stage application under 35 U.S.C. § 371 of International Application No. PCT/IB2017/057584, filed on Dec. 1, 2017, entitled, "RISK FACTOR MONITORING," which claims the benefit of and priority to U.S. Provisional Application No. 62/430,232, filed Dec. 5, 2016, entitled, "INTERTWINED ELECTRICAL INPUT SIGNALS," each of which is hereby incorporated by reference herein in its entirety.

FIELD OF THE PRESENT DISCLOSURE

The present disclosure relates generally to methods, systems, and devices for determining the presence of an endogenous species in a blood sample, such as a whole blood sample.

BACKGROUND

For diabetes care with blood glucose monitor (BGM) systems, reporting glucose concentration in a blood sample, such as a whole blood sample, alone is the normal practice. No attention is given to other species in the blood, such as interfering or non-interfering endogenous species, other than to improve the determination of the glucose concentration. Thus, additional information that can be extracted from the blood sample is lost.

Recent diabetes research shows several endogenous species and their relationship to the diabetes conditions. For example, recent studies indicate that a high level of uric acid is linked to the onset of diabetes and that high uric acid levels may even raise the chances of getting diabetes. Studies also have shown strong links between uric acid levels and metabolic syndrome, which is a combination of medical conditions that are related to insulin resistance (i.e., the body's inability to respond to and use the insulin it produces), and increase a person's chances of getting heart disease and diabetes. Other studies have shown the link between high cholesterol and triglyceride and the deterioration of diabetic conditions of people with diabetes.

Accordingly, methods, systems, and devices are needed that provide information on the endogenous species from samples used in the determination of glucose concentration.

SUMMARY

Aspects of the present disclosure include apparatuses, systems, and methods related to determining an analyte concentration, such as a glucose concentration, as well as reporting one or more parameters about, or concentrations of, the endogenous species within the sample. Endogenous species (i.e., chemical substances that are present naturally in the human body) include, for example, uric acid, dopamine, triglyceride, etc. and are within the blood sample. The apparatuses, systems, and methods also include logging the analyte concentration and the one or more parameters over time. The logging provides for patient profiling, which provides data in more than one dimension and can lead to additional therapeutic actions that address the long term health of the user from which the samples are withdrawn.

Aspects of the present disclosure further include apparatuses, systems, and methods for the determination and logging of risk factor parameters associated with a sample, in association with the measurement of a concentration of an analyte in the sample.

Further aspects of the present disclosure include a method of electrochemically analyzing a sample. The method includes applying an input signal, via an electrode, to the sample, where the input signal has at least one excitation. The method further includes measuring an output signal responsive to the input signal. The method also includes determining a concentration of an analyte within the sample based on the output signal. The method further includes determining at least one risk factor parameter associated with at least one species in the sample other than the analyte.

Further aspects of the present disclosure include a method of generating a patient profile. The method includes intertwining a first input signal, via a first electrode having a reagent, with a second input signal, via a second electrode lacking a reagent, or having a specific reagent for a different target species. The intertwining includes applying to the sample, via the first electrode, the first input signal having at least one excitation and a relaxation; and applying to the sample, via the second electrode, the second input signal having at least one excitation and a relaxation. Further, such applications occur such that the at least one excitation of the first input signal is nonconcurrent with the at least one excitation of the second input signal. The method further includes measuring a first output signal responsive to the first input signal and a second output signal responsive to the second input signal. The method further includes determining the concentration of the analyte based on at least the first output signal and the second output signal. The method also includes determining at least one risk factor parameter associated with at least one endogenous species in the sample based on at least the second output signal.

Additional aspects of the present disclosure include a method of analyzing a sample with a blood glucose monitoring device. The method includes applying an input signal to the sample via a bare electrode of the blood glucose monitoring device, in which the input signal includes a constant voltage pulse. The method further includes determining at least one risk factor parameter associated with at least one endogenous species in the sample other than glucose in response to the constant voltage pulse. The method also includes logging the at least one risk factor parameter within a patient profile stored in the blood glucose monitoring device.

Aspects of the present disclosure further include one or more devices and systems configured to perform or execute the methods described above. In some aspects, the one or more devices and one or more components of the systems include computer-readable instructions that cause the devices and the one or more components to execute operations of the methods described above.

Additional aspects of the present disclosure will be apparent to those of ordinary skill in the art in view of the detailed description of various embodiments, which is made with reference to the drawings, a brief description of which is provided below.

Figure 1:
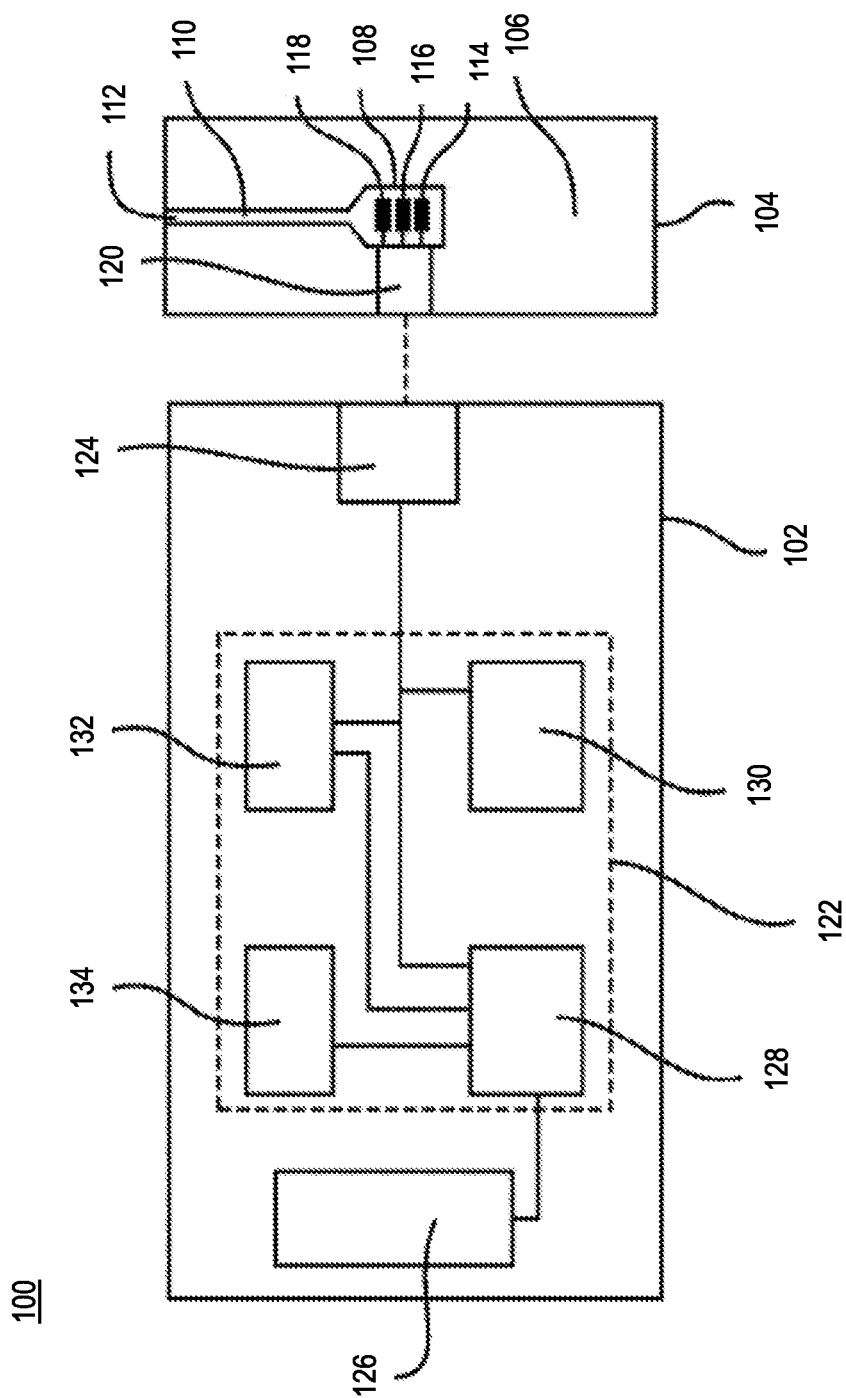
FIG. 1 depicts a schematic representation of a biosensor system, in accord with aspects of the present disclosure.

The present disclosure is susceptible to various modifications and alternative forms, and some representative embodiments have been shown by way of example in the drawings and will be described in detail herein. It should be understood, however, that the disclosure is not intended to be limited to the particular forms illustrated and described. Rather, the present application covers all modifications, equivalents, and alternatives falling within the spirit and scope of the present disclosure, as further defined by the appended claims.

DETAILED DESCRIPTION

While this disclosure is susceptible of embodiment in many different forms, there is shown in the drawings and will herein be described in detail example implementations of the inventions and concepts herein with the understanding that the present disclosure is to be considered as an exemplification of the principles of the inventions and concepts and is not intended to limit the broad aspect of the disclosed implementations to the examples illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." For purposes of the present detailed description and accompanying figures, terms defined below and used throughout that include numbers separated by commas or numbers separated by hyphens, but being otherwise identical, refer to the same term and such notations are interchangeable. For example, $i_{G1,1}$ is identical to $i_{G1\text{-}1}$.

The present disclosure includes methods, systems, and devices that provide biological sample profiling. The profiling includes conventional glucose concentration measurements. The profiling also includes the determination of parameters associated with, or concentrations of, one or more endogenous species in the blood sample, besides glucose. Profiling of the parameters (referred to below as risk factor parameters) provides greater insight into the total health of the user from which the samples are withdrawn, beyond just providing glucose concentrations. The risk factor parameters allow for the monitoring, diagnosis, and/or detection of medical conditions that before was not possible during glucose concentration measurements of blood samples.

Endogenous species are chemical substances that are present naturally in the human body. Such endogenous species can be any endogenous species found in a sample, such as a whole blood sample. For example, such endogenous species can be uric acid (UA), cholesterol (CH), triglyceride (TG), ascorbic acid (ASA), bilirubin (BRB), dopamine (Dop), hemoglobin (Hb), lactic acid (LA), and 3-hydroxybutyric acid or beta-hydroxybutyric acid (3-HBA) (or ketones in general), among others. As used herein, endogenous species also can refer to species that are present in the human body based on the consumption of a substance that results in the species being present in the body, such as in the case of acetaminophen (AA). The endogenous species referred to herein also may be referred to as risk factors because presence of the endogenous species alone, or at certain levels, indicates the risk or presence of certain medical conditions. The one or more parameters associated with the presence of concentration of the endogenous species may be referred to as risk factor parameters.

As briefly discussed above, the endogenous species uric acid, triglyceride, and cholesterol are commonly occurring endogenous species, with uric acid showing a link to diabetes and triglyceride and cholesterol showing a link to insulin resistance and diabetes complications. The endogenous species 3-HBA and lactate can be triggered by excessive fasting and moderate exercise, respectively. The determination of the risk factor parameters and/or concentrations of these endogenous species provides a more complete picture of the blood sample and provides information that a glucose concentration and/or percent hematocrit level cannot provide alone. The information can include signs that diabetes management is improving or worsening, which was conventionally not readily determined with the glucose concentration alone. Moreover, profiling the risk factor parameters over time also can provide insights into other conditions related to diabetes care management, such as insulin resistance and the like, that the profiling of glucose concentrations alone may not readily provide.

Reporting the determined concentration or one or more risk factor parameters of endogenous species along with the determined glucose concentration provides a profile of the whole blood sample for a user. This profiling provides a long term patient profile solution for a user, including providing a whole blood profile along with other patient information, reflecting the progressive change, or lack thereof, over time, which benefits the diabetes care/management. By logging multiple risk factor parameters along with the glucose concentrations in memory of a blood glucose monitoring device, or a remote device (e.g., cloud-base service, medical service, patient database, etc.), such as over a long period of time, individuals having various diabetic or pre-diabetic conditions can show different patterns that glucose concentration values alone could not show.

Although the focus of the present disclosure is on the sampling of blood, such as whole blood, the biological sample can be any biological sample, such as saliva, sweat, urine, breast milk, and the like. Further, although the present disclosure concerns primarily with the determination of a glucose concentration as the analyte in the biological sample, the analyte for which the concentration within the biological sample is determined can be various other analytes besides glucose.

FIG. 1 depicts a schematic representation of a biosensor system 100 that can determine one or more risk factor parameters of one or more endogenous species in a sample, such as a whole blood sample, and can create a profile that includes multiple risk factor parameters logged over time, in accord with aspects of the present disclosure. The biosensor system 100 includes a measurement device 102 and a test sensor 104, which can be implemented in an instrument, such as a portable or hand-held device, or the like. The measurement device 102 and the test sensor 104 can be adapted to implement an electrochemical sensor system or the like. The biosensor system 100 can be utilized to determine concentrations of one or more analytes within a sample, such as glucose, along with one or more risk factor parameters of endogenous species in the sample. The biosensor system 100 also can be utilized to log and track the glucose concentrations and the risk factor parameters overtime to create a profile of a user of the biosensor system 100. The profile provides, for example, information on diabetes care management. The information can include information on risk factors based on the risk factor parameters that can be used to adjust the diabetes care management and provide a more complete view of the patient health. While a particular configuration is shown, the biosensor system 100 can have other configurations, including those with or without additional components, without departing from the spirit and scope of the present disclosure. For example, in some embodiments, the biosensor system 100 may lack the working electrode or the bare electrode, as discussed further below.

The test sensor 104 has a base 106 that forms a reservoir 108 and a channel 110 with an opening 112. The reservoir 108 defines a partially-enclosed volume. The reservoir 108 can contain a composition that assists in retaining a liquid sample, such as water-swellable polymers or porous polymer matrices. The test sensor 104 can have other configurations without departing from the spirit and scope of the present disclosure. The test sensor 104 can be configured to analyze, for example, a single drop of whole blood, such as from 1-15 microliters (µL) in volume. In use, a liquid sample for analysis is transferred into the reservoir 108 by introducing the liquid to the opening 112. The liquid sample flows through the channel 110, filling the reservoir 108 while expelling the previously contained air.

The test sensor 104 can includes three electrodes, namely a working electrode 114, a counter electrode 116, and a bare electrode 118. However, in some aspects, the test sensor 104 can include a different number of electrodes, such as two electrodes, such as only the working electrode 114 and the counter electrode 116 or only the bare electrode 118 and the counter electrode 116, more than three electrodes, including more than one working electrode 114, more than one counter electrode 116, and/or more than one bare electrode 118. By way of example, and without limitation, the test sensor 104 can include two counter electrodes 116, with the two counter electrodes 116 separately paired with the working electrode 114 and the bare electrode 118.

The working electrode 114 can include one or more reagents, such as one or more enzymes, binders, mediators, and like species. One or more of the reagents react with and transfer electrons from the analyte during the analysis and, thus, facilitate in the redox reaction of an analyte within the sample. The measurement device 102 can then measure and record the electrons as current and/or voltage passing through the test sensor 104, and translate the current and/or voltage into a measure of the analyte concentration of the sample.

An enzyme or similar species included with the reagents enhances the electron transfer from a first species to a second species during the redox reaction. The enzyme or similar species may react with the analyte, thus providing specificity to a portion of the generated output signal. A mediator can be used to maintain the oxidation state of the enzyme. Thus, in the case of the working electrode 114 with the enzyme and the mediator, the working electrode 114 is where the analyte undergoes electrochemical reaction. The counter electrode 116 is where the opposite electrochemical reaction occurs, which allows current to flow between the working electrode 114 and the counter electrode 116. Thus, if oxidation occurs at the working electrode 114, reduction occurs at the counter electrode 116.

The binder included with the reagents can include various types and molecular weights of polymers, such as carboxyl methyl cellulose (CMC), HEC (hydroxyl ethyl cellulose), and/or polyethylene oxide (PEO). In addition to binding the reagents together, the binder can assist in filtering red blood cells, preventing or inhibiting them from coating the surface of the working electrode 114, such as in the case of a blood glucose monitoring device.

In contrast, the bare electrode 118 does not include the one or more reagents that facilitate in the redox reaction of an analyte that is the focus of the biosensor system. Thus, the bare or second electrode, as described and used herein, can be an electrode without any added reagent chemistry, or with one or more added inert materials. The bare electrode can also include added reagent chemistry that is not for the target analyte, in contrast to the working or first electrode described throughout as having reagent chemistry for the target analyte. Thus, although described as "bare," the bare electrode 118 merely does not include the same or identical one or more reagents that facilitate in the redox reaction of the analyte that are included on the working electrode 114. The bare electrode 118 can include other reagents that facilitate in the redox reaction of other species within the sample, besides the analyte of interest. Alternatively, the bare electrode 118 can merely be a bare conductor without any reagent whatsoever thereon or therein.

The bare electrode 118 can be arranged upstream from the working electrode 114 so that the effects of the one or more reagents on the working electrode 114 do not affect, or have minimal effect on, the electrical responses of the bare electrode 118. Alternatively, in some aspects, the working electrode 114 and the bare electrode 118 can be arranged in separate reservoirs 108 with substantial chemical isolation. Accordingly, the analyte that is the focus of the concentration determination of the biosensor system 100 responds to a current or voltage applied to the working electrode 114 based on the working electrode 114 having the one or more reagents. The analyte does not respond, or responds minimally, to a current or voltage applied to the bare electrode 118 based on the bare electrode 118 not having the one or more reagents.

In one embodiment, the electrodes 114-118 can be substantially in the same plane or in more than one plane. In one embodiment, the electrodes 114-118 can be disposed on a surface of the base 106 that forms the reservoir 108. In one embodiment, the electrodes 114-118 can extend or project into the reservoir 108.

The test sensor 104 further includes a sample interface 120 that has conductors connected to the working electrode 114, the counter electrode 116, and the bare electrode 118. An output signal, such as a first output signal or a working output signal, can be measured from one or both of the conductors connected to the working electrode 114 and the counter electrode 116. Another output signal, such as a second output signal or a bare output signal, can be measured from one or both of the counter electrode 116 and the bare electrode 118.

The measurement device 102 includes electrical circuitry 122 connected to a sensor interface 124 and a display 126. The electrical circuitry 122 includes a processor 128 connected to a signal generator 130, an optional temperature sensor 132, and a storage medium 134. The display 126 can be analog or digital. The display 126 can include an LCD (liquid crystal display), an LED (light emitting device), an OLED (organic light emitting device), a vacuum fluorescent, electrophoretic display (ED), or other display adapted to show a numerical reading. Other electronic displays can be used. The display 126 electrically communicates with the processor 128. The display 126 can be separate from the measurement device 102, such as when in wireless communication with the processor 128. Alternatively, the display 126 can be removed from the measurement device 102, such as when the measurement device 102 electrically communicates with a remote computing device, medication dosing pump, and the like.

The signal generator 130 provides one or more electrical input signals to the sensor interface 124 in response to the processor 128. The electrical input signals can be transmitted by the sensor interface 124 to the sample interface 120 to apply the electrical input signals to the sample of the biological fluid. The electrical input signals can be a potential or a current and can be constant, variable, or a combination thereof, as further described below. The electrical input signals can be applied as a single pulse or in multiple pulses, sequences, or cycles. Thus, the electrical input signals can include the first and second input signals. The signal generator 130 also can record one or more output signals from the sensor interface 124 as a generator-recorder. Thus, the one or more output signals can include the first and second output signals. Although generally disclosed throughout as intertwined input signals from two or more electrodes, the signal generator 130 can generate one input signal rather than multiple intertwined inputs signals.

The optional temperature sensor 132 determines the temperature of the biosensor system, including the device and the sample in the reservoir 108 of the test sensor 104. The temperature of the sample can be measured, calculated from the output signal, or assumed to be the same or similar to a measurement of the ambient temperature or the temperature of a device implementing the biosensor system 100. The temperature can be measured using a thermistor, thermometer, or other temperature sensing device. Other techniques can be used to determine the sample temperature.

The storage medium 134 can be a magnetic, optical, or semiconductor memory, another electronic storage device, or the like. The storage medium 134 can be a fixed memory device, a removable memory device, such as a memory card, remotely accessed, or the like. The storage medium can be used to log the analyte concentrations and the one or more risk factor parameters.

The electronic processor 128 implements the analyte analysis and data treatment using computer-readable software code and data stored in the storage medium 134. The processor 128 can start the analyte analysis and data treatment in response to the presence of the test sensor 104 at the sensor interface 124, the application of a sample to the test sensor 104, in response to user input, or the like. The processor 128 directs the signal generator 130 to provide the electrical input signals to the sensor interface 124. The processor 128 receives the output signals from the sensor interface 124. At least some of the output signals are generated in response to the input signals applied to the sample. Other output signals can be generated based on other characteristics, such as the temperature of the sample. In response to the output signals, the processor 128 determines an analyte concentration and one or more risk factor parameters. Thus, in response to the output signals, including the same output signals used to determine the analyte concentration, the processor 128 can determine one or more risk factor parameters associated with one or more endogenous species within the sample. Determination of the analyte concentration and the risk factor parameters is based one or more analyte concentration correlations and one or more risk factor correlations stored in the biosensor system 100 that are functions of at least portions of the output signals.

Applying the input signals to a test strip through the biosensor system 100 provides information about the target analyte concentration and the risk factor parameters. The information can be logged each time the biosensor system 100 analyzes a sample to generate a profile, such as logged in the storage medium 134 or a remote storage medium. The profile allows the analyte concentration and the risk factor parameters to be tracked over time. Thus, the profile provides improved healthcare management of a patient and can provide insights that the analyte concentration alone, or even logging of the analyte concentration alone, cannot provide.

Figure 2:
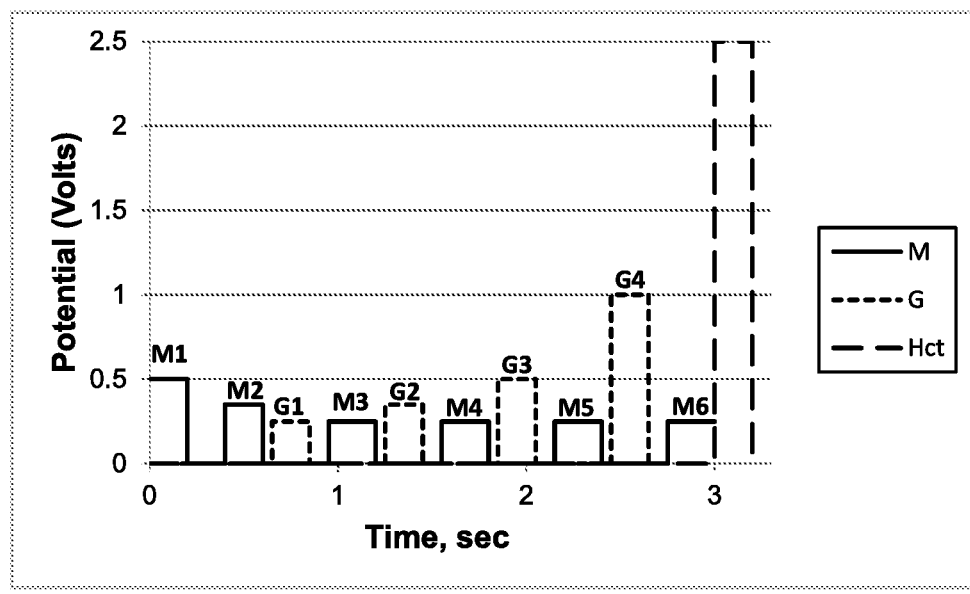
FIG. 2 is a graph illustrating an application of intertwined input signals for a biosensor system, in accord with aspects of the present disclosure.

FIG. 2 is a graph illustrating exemplary intertwined input signals for an electrochemical biosensor system, such as the system 100 of FIG. 1, in accord with aspects of the present disclosure. The intertwined input signals include three input signals represented by the labels M, G, and Hct. As described in relation to the biosensor system 100 of FIG. 1, the first input signal M includes electrical pulses (or simply pulses) of constant potential (voltage) applied across the working electrode 114 and the counter electrode 116. However, the first input signal can be applied to any biosensor system with a working electrode and a counter electrode as described herein. In some aspects, the first input signal can be described as a working input signal based on the signal being applied to the sample via the working electrode 114.

As shown, the first input signal M includes six pulses, which will be referred to here in the order in which they appear from left to right on the graph as $M_1$, $M_2$, $M_3$, $M_4$, $M_5$, and $M_6$. The pulse $M_1$ has a potential of 0.5 volt (V), the pulse $M_2$ has a potential of 0.35 V, and the remaining pulses $M_3$ to $M_6$ have potentials of 0.25 V. Because the pulses of the first input signal M are applied via the working electrode 114 with the one or more reagents, the pulses of the first input signal M generally probe the analyte in the sample, either directly or indirectly through a mediator or other measurable species. However, in some embodiments, the pulses of the first input signal can also probe the endogenous species in the sample.

The second input signal G also includes pulses of constant potential. However, as described in relation to the biosensor system 100 of FIG. 1, the pulses of the second input signal G are applied across the bare electrode 118 and the counter electrode 116. However, the second input signal can be applied to any biosensor system with a bare electrode and a counter electrode as described herein. In some aspects, the second input signal can be described as a bare input signal because the second input signal is applied via the bare electrode 118.

As shown, the second input signal G includes four pulses, which will be referred to here in the order in which they appear from left to right on the graph as $G_1$, $G_2$, $G_3$, and $G_4$. The pulse $G_1$ has a potential of 0.25 V, the pulse $G_2$ has a potential of 0.35 V, the pulse $G_3$ has a potential of 0.5 V, and the pulse $G_4$ has a potential of 1.0 V. Because the bare electrode 118 does not include one or more reagents that are responsive to the target analyte within the sample, the pulses of the second input signal G applied via the bare electrode 118 generally do not probe the target analyte targeted by the working electrode 114 in the sample. Instead, the pulses of the second input signal G applied via the bare electrode 118 probe the other species in the sample across the electrochemical detection window, such as the endogenous species. Thus, measurements based on the bare electrode 118 are sensitive mostly to other oxidizable species at various potentials and not the target analyte being analyzed by the first input signal M and the working electrode 114. However, measurements based on the working electrode 114 can be used to probe the other species in the sample across the electrochemical detection window besides only the intended analyte. Further, measurements based on the working electrode 114 and the bare electrode 118 can be used in combination to probe the other species in the sample across the electrochemical detection window.

The third input signal Hct is a single pulse for determining the hematocrit level of the sample, in the case of a whole blood sample. As described in relation to the biosensor system 100 of FIG. 1, the single pulse of the third input signal Hct is a constant voltage of 2.5 V applied across the bare electrode 118 and the combination of the counter electrode 116 and the working electrode 114. Alternatively, the single pulse of the third input signal Hct instead can be applied across the bare electrode 118 and the counter electrode 116, with the working electrode 114 in an open state.

As shown, the pulses of the first and second input signals are nonconcurrent (i.e., the first and second signals are not maximally energized at the same time, or no maximum voltage of the first input signal overlaps any maximum voltage of the second input signal). Moreover, each pulse of the first input signal is separated by the next pulse of the first input signal by a pulse of the second input signal. Based on the pulses of the first and second input signals being nonconcurrent, and a pulse of the second input signal separating the pulses of the first input signal, the pulses of the first and second input signals are described as being intertwined.

When not applying a voltage pulse, the working electrode 114 and the bare electrode 118 can be in an open circuit state. Thus, during pulses of the first input signal, the bare electrode 118 can be in an open circuit state, and during pulses of the second input signal, the working electrode 114 can be in an open circuit state.

As shown, each pulse of the first and second input signals is followed by an electrical relaxation, or simply a relaxation. Specifically, each pulse of the first input signal is immediately followed by a relaxation, such as no input potential (or open circuit), for the first input signal, and each pulse of the second input signal is immediately followed by a relaxation, such as zero potential (or open circuit), for the second input signal. The periods between pulses of the same input signal can be considered relaxations of that particular signal. The periods between pulses of all input signals, i.e., where there is no pulse, can be considered relaxations of the system 100. Thus, after a pulse of the first input signal is a relaxation of the first input signal until the next pulse of the first input signal. As shown in FIG. 2, after a pulse of the first input signal is a relaxation of the system until the next pulse of the second input signal. The combination of a pulse followed by a relaxation within the first or second input signal can be a duty cycle. The first and second input signals, therefore, can include a plurality of duty cycles of pulses followed by relaxations.

Although described as the working electrode 114 or the bare electrode 118 being in an open state during a relaxation, or having a zero potential applied across the working electrode 114 and/or bare electrode 118, the relaxations of the working electrode 114 and the bare electrode 118 do not require that the electrodes 114 and 118 be in an open state. In some aspects, a current passing through the working electrode 114 and the bare electrode 118 can be at least half as much current as in a closed state and still be considered in a relaxation period. Alternatively, a working or bare electrode can be considered to be in a relaxation period or state when the potential applied to the electrode is lower than a redox potential of the target analyte or species, as the case may be. Alternatively, a working or bare electrode can be considered to be in a relaxation period or state when the current is reduced to at least one-half the current flow at the excitation maxima or by at least an order of magnitude in relation to the current flow at the excitation maxima.

Further, relaxation, as described and used herein, can mean that the electrode of interest has no input signal for excitation, such as in the case of an open circuit. Relaxation can also mean that the biosensor system, as a whole, has no input signal for all electrodes. During intertwining, one electrode can be in relaxation while the other electrode is in excitation, and vice versa. However, the biosensor system cannot be in relaxation until both electrodes (or all electrodes, in the case of more than two electrodes) are in relaxation. For the working electrode having added reagent chemistry for the target analyte the relaxation for that particular electrode is the incubation time where the measurable species is generated from the enzyme activated chemical reaction without external influence, such as the electrochemical reaction. For the working electrode having no added reagent chemistry for the target analyte, as discussed in detail below, the relaxation time of the electrode is when all electrochemically active species (oxidizable and reducible) replenish by diffusion to a depletion layer during the input of a signal to the electrode.

Each pulse, as well as each relaxation, has a width, also referred to as a pulse width and a relaxation width, respectively. A pulse and relaxation pair defines a duty cycle. For each duty cycle, the pulse and relaxation widths combined are a duty cycle width or duty cycle period. The pulse widths for the pulses of the first input signal can all have the same width, can all have different widths, or can have combinations of the same and different widths. Similarly, the relaxation widths for the relaxations of the first input signal can all have the same width, can all have different widths, or can have combinations of the same and different widths. The pulse widths and the relaxation widths of the duty cycles of the first input signal can be the same width or can be different widths. In addition, the widths or periods of the duty cycle of the first input signal can be the same width or be different widths.

Similarly, the pulse widths for the pulses of the second input signal can all have the same width, can all have different widths, or can have combinations of the same and different widths. Similarly, the relaxation widths for the relaxations of the second input signal can all have the same width, can all have different widths, or can have combinations of the same and different widths. The pulse widths and the relaxation widths of the duty cycles of the second input signal can be the same width or can be different widths. In addition, the widths or periods of the duty cycle of the second input signal can be the same width or be different widths. Again, according to some aspects, the application of maximum electrical energy to the first and second input signals occurs non-concurrently. What is emphasized is that the electrical energy applied to the electrodes according to the present disclosure is not necessarily limited to any particular shape, amplitude, or duration.

For the first input signal shown in FIG. 2, the pulse widths of the pulses $M_1$ and $M_2$ are 0.2 second (s) and the pulse widths of the pulses $M_3$, $M_4$, $M_5$, and $M_6$ are 0.25 s. For the second input signal, the pulse widths for the pulses $G_1$, $G_2$, $G_3$, and $G_4$ are 0.2 s. The relaxation widths of the first input signal are 0.2 s, 0.35 s, 0.35 s, 0.35 s, and 0.35 s after the pulses $M_1$-$M_5$, respectively. The relaxation widths of the second input signal are 0.4 s, 0.4 s, 0.4 s, and 0.35 s after the pulses $G_1$-$G_4$, respectively. The pulse width of the hematocrit pulse is 0.2 s.

Figure 3:
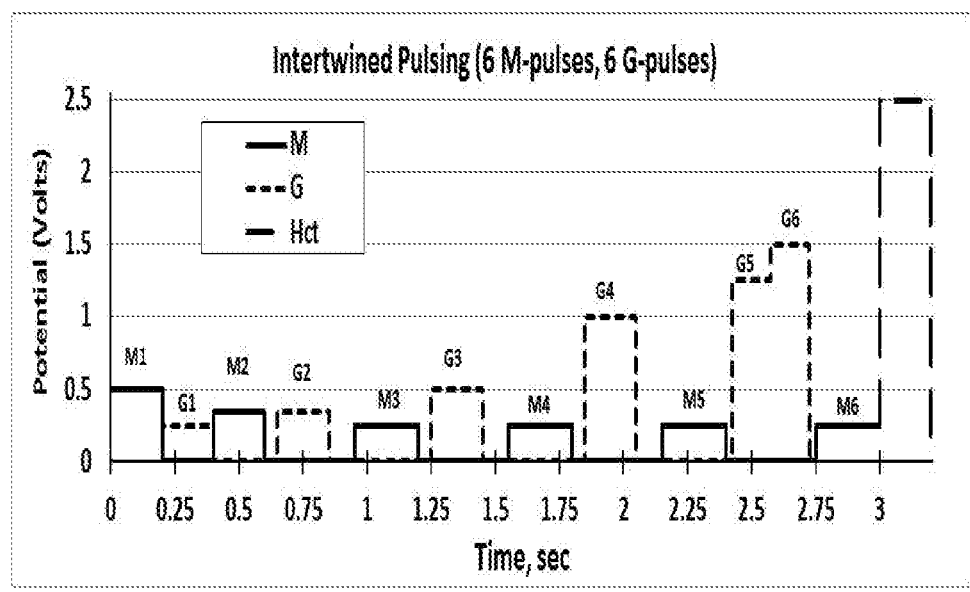
FIG. 3 is a graph illustrating another application of intertwined input signals for a biosensor system, in accord with aspects of the present disclosure.

FIG. 3 is another graph illustrating exemplary intertwined input signals for an electrochemical biosensor system, such as the system 100 of FIG. 1, in accord with aspects of the present disclosure. Like FIG. 2 above, FIG. 3 shows three input signals, represented by the labels M, G, and Hct. As described in relation to the biosensor system 100 of FIG. 1, the first input signal M includes pulses of constant potential applied across the working electrode 114 and the counter electrode 116. However, the first input signal can be applied to any biosensor system with a working electrode and a counter electrode as described herein. In some aspects, the first input signal can be described as a working input signal based on the signal being applied to the sample via the working electrode 114.

As shown, the first input signal M includes six pulses, which will be referred to here in the order in which they appear from left to right on the graph as $M_1$, $M_2$, $M_3$, $M_4$, $M_5$, and $M_6$. The pulse $M_1$ has a potential of 0.5 volt (V), the pulse $M_2$ has a potential of 0.35 V, and the remaining pulses $M_3$ to $M_6$ have potentials of 0.25 V. Because the pulses of the first input signal M are applied via the working electrode 114 with the one or more reagents, the pulses of the first input signal M generally probe the analyte in the sample, either directly or indirectly through a mediator or other measurable species.

The second input signal G also includes pulses of constant potential. As described in relation to the biosensor system 100 of FIG. 1, the pulses of the second input signal G are applied across the bare electrode 118 and the counter electrode 116. However, the second input signal can be applied to any biosensor system with a bare electrode and a counter electrode as described herein. In some aspects, the second input signal can be described as a bare input signal because the second input signal is applied via the bare electrode 118.

As shown, the second input signal G includes six pulses, which will be referred to here in the order in which they appear from left to right on the graph as $G_1$, $G_2$, $G_3$, $G_4$, $G_5$, and $G_6$. The pulse $G_1$ has a potential of 0.25 V, the pulse $G_2$ has a potential of 0.35 V, the pulse $G_3$ has a potential of 0.5 V, the pulse $G_4$ has a potential of 1.0 V, the pulse $G_5$ has a potential of 1.3 V, and the pulse $G_6$ has a potential of 1.5 V. Because the bare electrode 118 does not include one or more reagents that are responsive to the target analyte within the sample, the pulses of the second input signal G applied via the bare electrode 118 generally do not probe the target analyte targeted by the working electrode 114 in the sample. Instead, the pulses of the second input signal G applied via the bare electrode 118 probe the other species in the sample across the electrochemical detection window, such as the endogenous species. Thus, measurements based on the bare electrode 118 are sensitive mostly to other oxidizable species at various potentials and not the target analyte being analyzed by the first input signal M and the working electrode 114, such as glucose. However, as discussed above, measurements based on the working electrode 114 also can be used to probe the other species in the sample across the electrochemical detection window besides only the intended analyte. Further, measurements based on the working electrode 114 and the bare electrode 118 can be used in combination to probe the other species in the sample across the electrochemical detection window.

FIGS. 2 and 3 illustrate just two examples of input signals that can be used to measure an analyte in a sample, such as glucose in a blood sample, along with determining one or more risk factor parameters from the sample. In a more general case, the first and second input signals can have fewer pulses, while still including intertwined first and second input signals. Also, other input signals can be used without departing from the spirit and scope of the present disclosure, and the other input signals can be applied using a different biosensor system. For example, the working input signal and the bare input signal can be applied in a non-intertwined arrangement. Alternatively, only one of the working and bare input signals can be applied. For example, a biosensor system may lack the working or bare electrode such that an input signal is applied via only the remaining one of a bare or working electrode. Thus, the present disclosure is not limited to only intertwined working and bare input signals, and is not limited to only being applied using the biosensor system 100. Thus, the detection of various endogenous species can rely on inputs and outputs from the working and/or bare electrodes. The detection of various endogenous species also can rely on input pulses at one or more specific voltages, can rely on one or more pulsing current decay behaviors, and/or the intermediate currents from various pulsing. To do so, one or more output signals are measured in response to the input signals.

Figure 4:
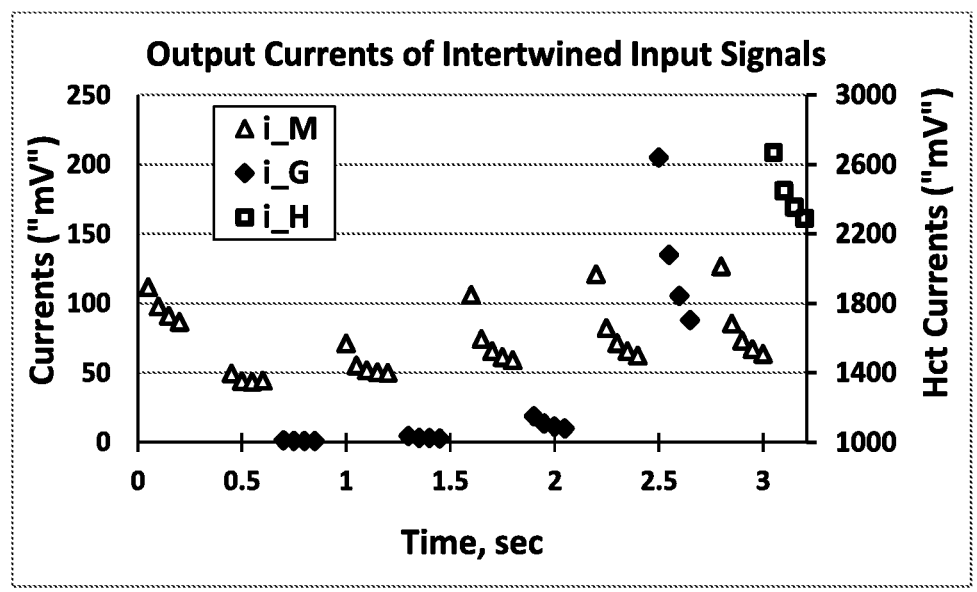
FIG. 4 is a graph illustrating first and second output signals measured in response to the first and second input signals of FIG. 2, in accord with aspects of the present disclosure.

FIG. 4 is a graph illustrating first and second output signals measured in response to the first and second input signals of FIG. 2, in accord with aspects of the present disclosure. The plotted values are currents recorded in the raw signal units of mV, which is proportional to the current unit of μA with a known electrical gain. Based on the first and second input signals being constant voltages applied across the respective electrode pairs, the first and second output signals represent amperometric measurements of the resultant output currents of the sample responsive to the first and second input signals. However, input signals can be applied that result in voltammetric measurements of the corresponding output signals. Any number of current measurements or values can be measured in response to each one of the pulses of the first and second input signals. For convenience of explanation, and as shown in FIG. 4, the specific number of currents described below was measured in response to the pulses of the first and second input signals.

With respect the first output signal, four output currents were measured in response to the first two M pulses, $M_1$ and $M_2$, and five output currents were measured in response to the last four M pulses, $M_3$-$M_6$. These output currents are designated according to the scheme $i_{MN,L}$, where i represents a current, M represents that the current is responsive to the first input signal, N represents the pulse number of the input signal, and L represents the current or measurement number for that particular pulse number. Thus, for example, $i_{M1,1}$ represents the first current for the first pulse of the first input signal, and $i_{M6,5}$ represents the fifth current for the sixth pulse of the first input signal.

With respect to the second output signal, four currents were measured in response to the first four G pulses $G_1$-$G_4$. These currents are designated according to the scheme $i_{GN,L}$, where i represents a current, G represents that the current is responsive to the second input signal, N represents the pulse number of the input signal, and L represents the current or measurement number for that particular pulse number. Thus, for example, $i_{G2,2}$ represents the second current for the second pulse of the second input signal, and $i_{G3,4}$ represents the fourth current for the third pulse of the second input signal.

With respect to the hematocrit determination of the third input signal, four current values were measured in response to the single pulse Hct. These currents are designated according to the scheme $i_{Hct,L}$, where i represents a current, Hct represents that the current is related to the hematocrit value, and L represents the current or measurement number for the hematocrit pulse.

Because the bare electrode 118 does not have a reagent that facilitates an oxidation or reduction of the target analyte whose concentration is sought to be measured, the current measurements were relatively constant in response to the second input signal, as shown in FIG. 4. Instead, the current measurements were indicative mostly of species in the sample that are unrelated to the oxidization of the analyte, such as the endogenous species. Further, by applying voltage pulses to the sample at varying potentials for the second input signal, oxidizable species at various potentials were sampled, such as the endogenous species. Thus, the voltage pulses of the bare electrode 118 during the second input signal sensed a different species of the sample in a whole blood sample than the analyte sensed by the working electrode 114 during the first input signal, and probe the whole blood environment profile through varying potential pulses, including probing the endogenous species. However, the voltage pulses of the working electrode 114 can also probe the endogenous species within the whole blood sample.

According to the foregoing measurements, the first and second input signals, either alone or used in combination, can be used to generate the risk factor parameters. The risk factor parameters determine the presence of the endogenous species in the sample and, in some cases, relate to or even determine the concentration of the endogenous species. The risk factor parameters can be various types of parameters depending on the particular endogenous species being probed. For example, in some aspects, one or more currents of the first output signal and the second output signal can be risk factor parameters. Additionally, or in the alternative, ratios of the currents of the first output signal, the second output signal, and/or the first output signal relative to the second output signal can be the risk factor parameters. Risk factor parameters based on the first or second output signal can be based on intra-pulse ratios or inter-pulse ratios.

Intra-pulse ratios are ratios based on current measurements in response to the same pulse. For example, intra-pulse ratios based on current measurements of the first output signal are designated according to the scheme $R_N = i_{MN,nth}/i_{MN,1st}$, where $R_N$ represents an intra-pulse ratio for pulse N of the first output signal, nth represents the last current for the pulse N, and 1st represents the first current for the pulse N. Referring back to FIG. 4, as an example, the first output signal would include six intra-pulse ratios of $R_1 = i_{M1,4}/i_{M1,1}$, $R_2 = i_{M2,4}/i_{M2,1}$, $R_3 = i_{M3,5}/i_{M3,1}$, $R_4 = i_{M4,5}/i_{M4,1}$, $R_5 = i_{M5,5}/i_{M5,1}$, and $R_6 = i_{M6,5}/i_{M6,1}$ for the six pulses of the first input signal.

Intra-pulse ratios based on current measurements of the second output signal are designated according to the scheme $RG_N = i_{GN,nth}/i_{GN,1st}$, where RGN represents an intra-pulse ratio for pulse N of the second output signal, and the remaining variables represent the similar values listed above for the intra-pulse ratio of the first output signal. Referring again to FIG. 4, the second output signal would include four intra-pulse ratios of $RG_1 = i_{G1,4}/i_{G1,1}$, $RG_2 = i_{G2,4}/i_{G2,1}$, $RG_3 = G_{3,4}/i_{G3,1}$, and $RG_4 = G_{4,4}/i_{G4,1}$ for the four pulses of the second output signal.

Inter-pulse ratios are ratios based on current measurements in response to the same signal but different pulses within the signal. For example, inter-pulse ratios based on current measurements of the first output signal are designated according to the scheme $R_{NO}=i_{MN,nth}/i_{MO,nth}$, where $R_{NO}$ represents the inter-pulse ratio for pulse N relative to pulse O of the first output signal, and nth is the last current for both pulse N and pulse O. Referring to FIG. 4, the first output signal would include inter-pulse ratios of $R_{21}=i_{M2,4}/i_{M1,4}$, $R_{31}=i_{M3,5}/i_{M1,4}$, $R_{32}=i_{M3,5}/i_{M2,4}$, $R_{41}=i_{M4,5}/i_{M1,4}$, $R_{42}=i_{M4,5}/i_{M2,4}$, $R_{43}=i_{M4,5}/i_{M3,5}$, $R_{51}=i_{M5,5}/i_{M1,4}$, $R_{52}=i_{M5,5}/i_{M2,4}$, $R_{53}=i_{M5,5}/i_{M3,5}$, $R_{54}=i_{M5,5}/i_{M4,5}$, $R_{61}=i_{M6,5}/i_{M1,4}$, $R_{62}=i_{M6,5}/i_{M2,4}$, $R_{63}=i_{M6,5}/i_{M3,5}$, $R_{64}=i_{M6,5}/i_{M4,5}$, and $R_{65}=i_{M6,5}/i_{M5,5}$. Other inter-pulse ratio types can include the ratio of the first current of a pulse to the ending current of another pulse, and the ratio of the ending current of a pulse to the first current of another pulse, or the like. Examples of these inter-pulse ratio types are $R'_{21}=i_{M2,1}/i_{M1,4}$, and $R''_{21}=i_{M2,4}/i_{M1,1}$.

Inter-pulse ratios based on current measurements of the second output signal are designated according to the scheme $RG_{NO}=i_{GN,nth}/i_{GO,nth}$, where $RG_{NO}$ represents the inter-pulse ratio for pulse N relative to pulse O of the second output signal, and the remaining variables represent the values listed above for the intra-pulse ratio of the first output signal. Referring to FIG. 4, the second output signal would include the inter-pulse ratios of $RG_{21}=i_{G2,4}/i_{G1,4}$, $RG_{31}=i_{G3,5}/i_{G1,4}$, $RG_{32}=i_{G3,5}/i_{G2,4}$, $RG_{41}=i_{G4,5}/i_{G1,4}$, $RG_{42}=i_{G4,5}/i_{G2,4}$, $RG_{43}=i_{G4,5}/i_{G3,5}$, $RG_{51}=i_{G5,5}/i_{G1,4}$, $RG_{52}=i_{G5,5}/i_{G2,4}$, $RG_{53}=i_{G5,5}/i_{G3,5}$, $RG_{54}=i_{G5,5}/i_{G4,5}$, $RG_{61}=i_{G6,5}/i_{G1,4}$, $RG_{62}=i_{G6,5}/i_{G2,4}$, $RG_{63}=i_{G6,5}/i_{G3,5}$, $RG_{64}=i_{G6,5}/i_{G4,5}$, and $RG_{65}=i_{G6,5}/i_{G5,5}$.

Ratios based on the first and second output signals are considered intertwined pulse ratios. Intertwined pulse ratios based on current measurements of the first output signal and the second output signal are designated according to the scheme $M_N G_O=i_{MN,nth}/i_{GN,nth}$, where $M_N$ is pulse N of the first output signal, $G_N$ is pulse O of the second output signal, and nth represents the last current measurement for the pulse N or O. Thus, for example, the intertwined pulses would include $M_1G_1=i_{M1,4}/i_{G1,4}$, $M_1G_2=i_{M1,4}/i_{G2,4}$, $M_1G_3=i_{M1,4}/i_{G3,4}$, $M_1G_4=i_{M1,4}/i_{G4,4}$, $M_2G_1=i_{M2,4}/i_{G1,4}$, $M_2G_2=i_{M2,4}/i_{G2,4}$, $M_2G_3=i_{M2,4}/i_{G3,4}$, $M_2G_4=i_{M2,4}/i_{G4,4}$, $M_3G_1=i_{M3,5}/i_{G1,4}$, $M_3G_2=i_{M3,5}/i_{G2,4}$, $M_3G_3=i_{M3,5}/i_{G3,4}$, $M_3G_4=i_{M3,5}/i_{G4,4}$, $M_4G_1=i_{M4,5}/i_{G2,4}$, $M_4G_2=i_{M4,5}/i_{G2,4}$, $M_4G_3=i_{M4,5}/i_{G3,4}$, $M_4G_4=i_{M4,5}/i_{G4,4}$, $M_5G_1=i_{M5,5}/i_{G1,4}$, $M_5G_2=i_{M5,5}/i_{G2,4}$, $M_5G_3=i_{M5,5}/i_{G3,4}$, $M_5G_4=i_{M5,5}/i_{G4,4}$, $M_6G_1=i_{M6,5}/i_{G1,4}$, $M_6G_2=i_{M6,5}/i_{G2,4}$, $M_6G_3=i_{M6,5}/i_{G3,4}$, and $M_6G_4=i_{M6,5}/i_{G4,4}$.

Thus, one or more of the intra-pulse ratios and the inter-pulse ratios for the first and second output signals, and the intertwined pulse ratios between the first and second output signals, can be risk factor parameters used in the determination of the presence of endogenous species. These risk factor parameters also can correlate to concentrations of the endogenous species and can be logged to track and monitor medical conditions related to the analyte concentration, such as diabetes care management, or other conditions, such as gout, as discussed further below.

Figure 5A:
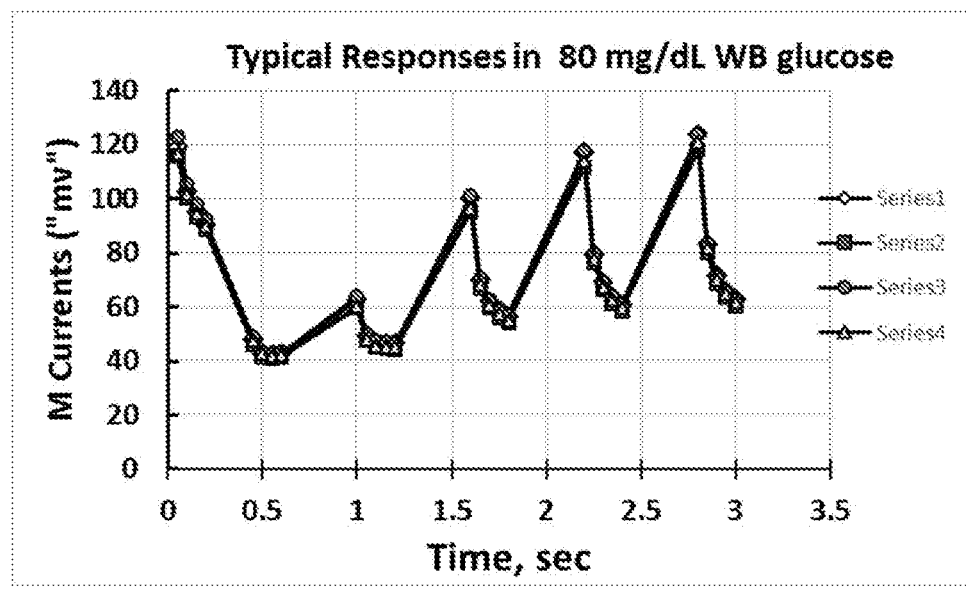
FIG. 5A is a graph illustrating an output signal measured in response to the input signal of the M pulses of FIG. 3 as applied to a blood sample with a glucose concentration of 80 mg/dL, in accord with aspects of the present disclosure.
Figure 5B:
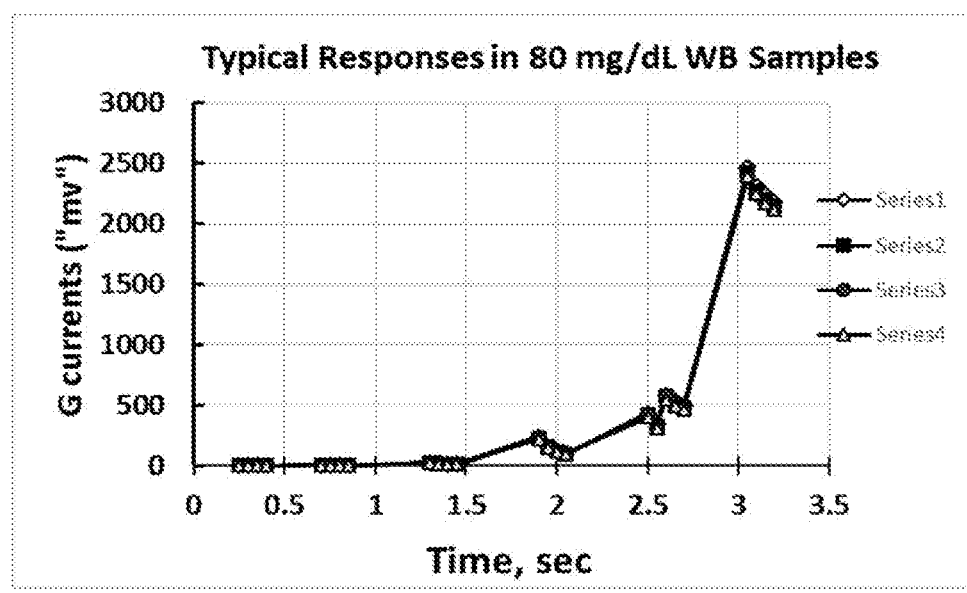
FIG. 5B is a graph illustrating an output signal measured in response to the input signal of the G pulses of FIG. 3 as applied to a blood sample with a glucose concentration of 80 mg/dL, in accord with aspects of the present disclosure.

Similar to FIG. 4, FIG. 5A illustrates exemplary responses to the M pulses of FIG. 3 as applied to a whole blood sample having 80 mg/dL of glucose (e.g., whole blood sample Series 1-4), in accord with aspects of the present disclosure. The plotted values are currents recorded in the raw signal units of mV, which is proportional to the current unit of μA with a known electrical gain. In response to the six M pulses $M_1$-$M_6$, four current measurements were taken for pulses $M_1$ and $M_2$, and five current measurements were taken for pulse $M_3$-$M_6$. The ending current of M pulse 6, or currents of other pulses, may be used as representative signals for the determination of the glucose concentration. With conversion functions and compensation methods, such as slope-based compensation, as disclosed in U.S. patent application Ser. Nos. 12/329,698 and 13/117,872, each of which is incorporated by reference herein in its entirety, complex index compensation, as disclosed in U.S. patent application Ser. No. 13/153,793, which is incorporated by reference herein in its entirety, and/or residual error compensation, as disclosed in U.S. patent application Ser. No. 13/053,722, which is incorporated by reference herein in its entirety, as well as using intertwined or separate current measurements from the G pulses, accurate glucose values can be determined from the glucose representative signals and the intermediate signals. FIG. 5B illustrates exemplary current responses to the G pulses of FIG. 3 as applied to a whole blood sample having the same baseline glucose. In response to the six G pulses $G_1$-$G_6$, four current measurements were taken for pulses $G_1$-$G_4$ and two and three current measurements were taken for pulse $G_5$ and $G_6$, respectively. The same intra- and inter-pulse ratios can be determined from the current measurements illustrated in FIG. 5 as discussed above in relation to FIG. 4.

FIGS. 2-5 illustrate only two of the many possible plots of the first and second input signals and the corresponding first and second output signals. The characteristics of the first and second input signals and resulting first and second output signals can be varied according to any of the above-described variations. Moreover, the input and output signals illustrated in FIGS. 2-5 are for explanation purposes and are not meant to be limiting. The risk factor parameters described herein can be determined without applying and/or measuring the entire input and output signals disclosed, or can be determined by applying different input and/or output signals.

As applied to determining risk factor parameters from the output signals for the endogenous species, there generally can be three basic current profiles resulting from the G pulses: (1) those having positive currents at low and high voltages as a result of direct oxidation of the endogenous species; (2) those having no or low direct oxidation currents at low to medium voltages and only finite amounts of positive oxidation currents at higher voltages; and (3) those having no direct oxidation currents but affecting the current decaying process within a pulse and/or having slight depression of currents compared to the currents without significant amount of species at higher voltages. Uric acid is representative of the first current profile associated with the first type of endogenous species. Beta-hydroxybutyric acid is representative of the second current profile associated with the third type of endogenous species. Triglyceride is representative of the second current profile associated with the third type of endogenous species. Each one of the types is discussed in greater detail below.

Two studies were carried out that show the ability to determine risk factor parameters related to the concentration of an endogenous species, specifically uric acid. A concentrated uric acid solution was spiked into whole blood samples having fixed baseline glucose concentrations such as 60, 80, 300, 400, and 550 mg/dL in different studies. The response currents from G pulsing were then compared to the baseline currents. Study 1 included baseline glucose concentrations of 80 and 300 mg/dL, added uric acid concentrations of 0, 5, 10, 20 and 30 mg/dL, a hematocrit level of 42%, and a temperature of 22±2° C. (RT). Study 2 included baseline glucose concentrations of 60 and 400 mg/dL, added uric acid concentrations of 0, 5, and 15 mg/dL, hematocrit levels of 25, 42, and 55%, and a target study temperature of 22±2° C. (RT).

Figure 6:
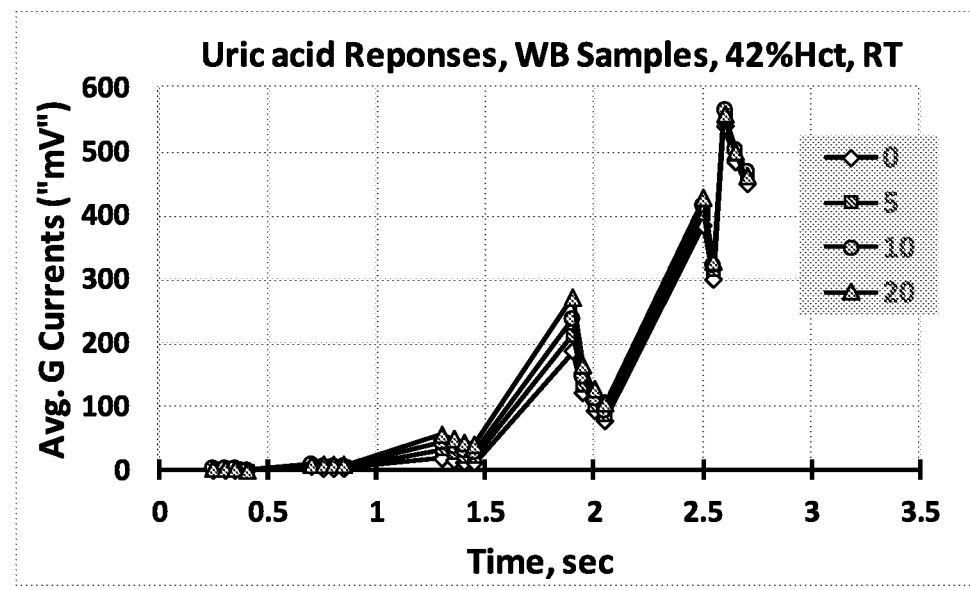
FIG. 6 is a graph illustrating average direct current profiles, according to the pulsing sequence in FIG. 3 with the G input signal, of blood samples containing added amounts of uric acid that are used to determine one or more risk factor parameters, in accord with aspects of the present disclosure.

Referring to FIG. 6, illustrated are the direct current profiles of the average G pulses for the samples containing added uric acid at concentrations of 0, 5, 10, 20 and 30 mg/dL in response to the input signal of FIG. 3. The response currents increase with increasing applied voltages progressively from 0.25 V to 0.35 V, 0.5 V, 1.0 V, 1.3 V, and 1.5 V in response to the G pulses 1, 2, 3, 4, 5 and 6, respectively. On top of the current profile from the baseline glucose (no added uric acid), increments of currents are visible for G pulses 3 and 4, but less so or no obvious increments may be seen at the G pulses 5 and 6. This is in part because uric acid begins to be oxidized at the lower voltage of 0.5 V, but the difference is less visible at higher voltages (e.g., 1.3 V and 1.5 V) when many other oxidizable species are also oxidized.

Figure 7:
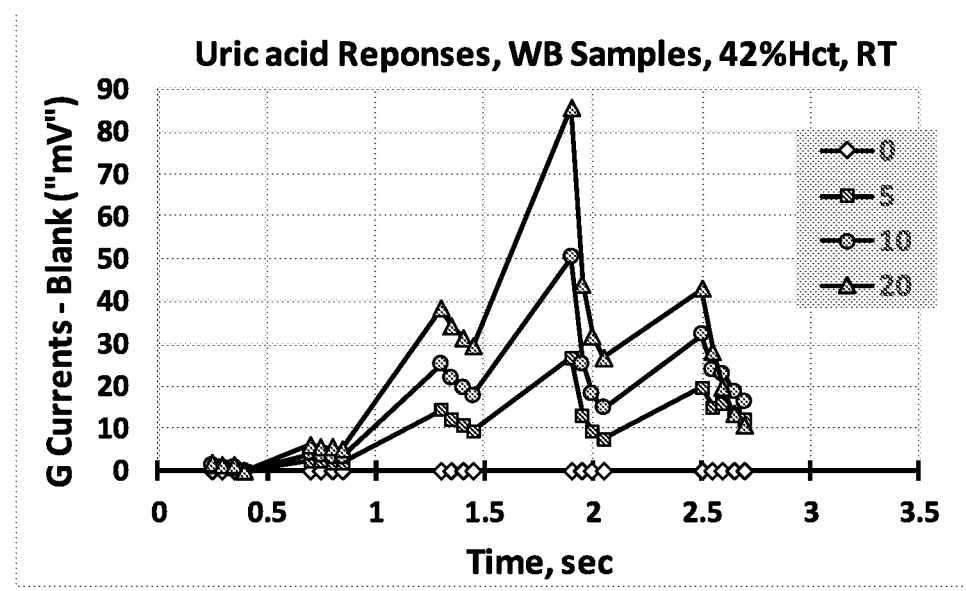
FIG. 7 is a graph illustrating normalized direct current profiles of samples from FIG. 6 containing uric acid that are used to determine one or more risk factor parameters, in accord with aspects of the present disclosure.

FIG. 7 illustrates the effect when the blank currents are subtracted off from the individual currents resulting from different added uric acid levels. Thus, the only effect illustrated in FIG. 7 is from the present uric acid, and the effect is more visible than in FIG. 6. Regardless of the initial pulsing, the ending currents for the G pulses at and after 0.5 V are virtually the same. This is a reflection of the diffusion-limited oxidation plateau for uric acid starting at 0.5 V. The diffusion-limited current for uric acid is basically unchanged at and after 0.5 V. At 0.35 V, uric acid is partially oxidized, as it is demonstrated in the figures. Accordingly, currents, intra-, and inter-pulse ratios based on the G pulse at 0.5 V in addition to other pulses, can be used for generating risk factor parameters associated with uric acid based on the pulses being responsive to the concentration of uric acid in the sample. The risk factor parameters can be generated from currents, intra-, or inter-pulse ratios based on the direct currents (FIG. 6) or baseline corrected currents (FIG. 7).

Figure 8:
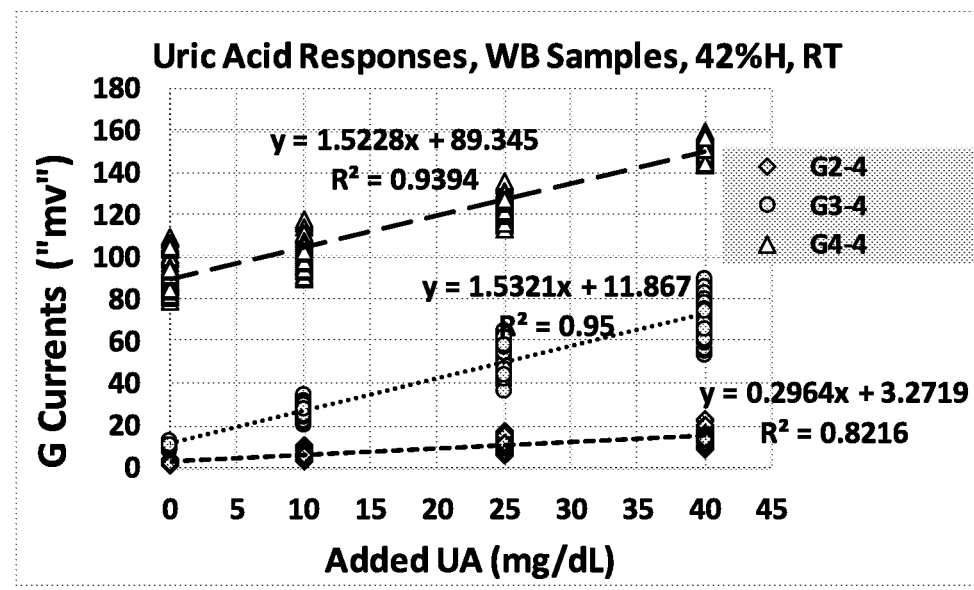
FIG. 8 illustrates exemplary risk factor parameters for uric acid from a uric acid study, in accord with aspects of the present disclosure.
Figure 9:
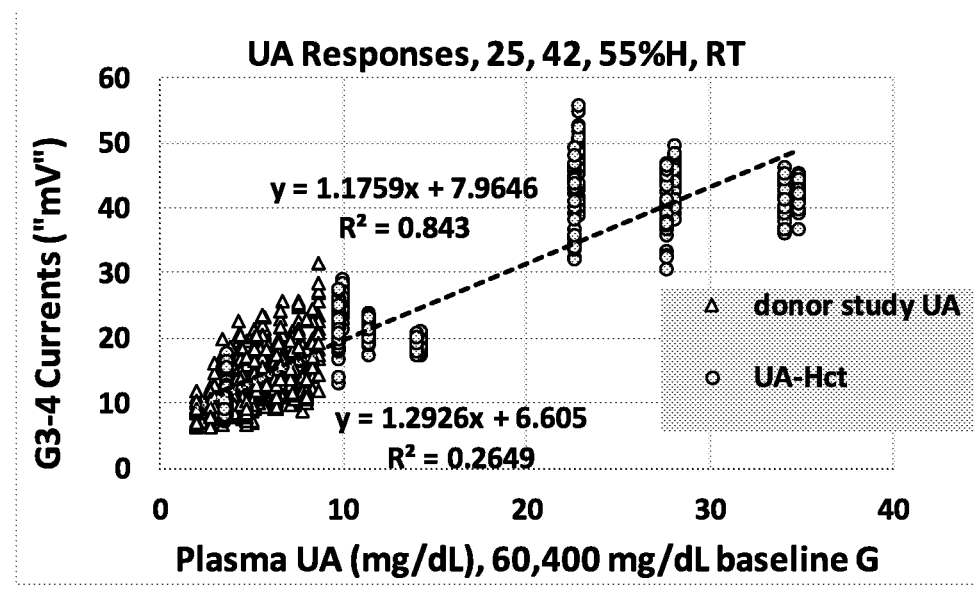
FIG. 9 illustrates correlation plots for the current $i_{G3\text{-}4}$ with the plasma uric acid concentrations from a study of uric acid at three hematocrit levels and for currents with determined uric acid concentrations from a donor study, in accord with aspects of the present disclosure.
Figure 10:
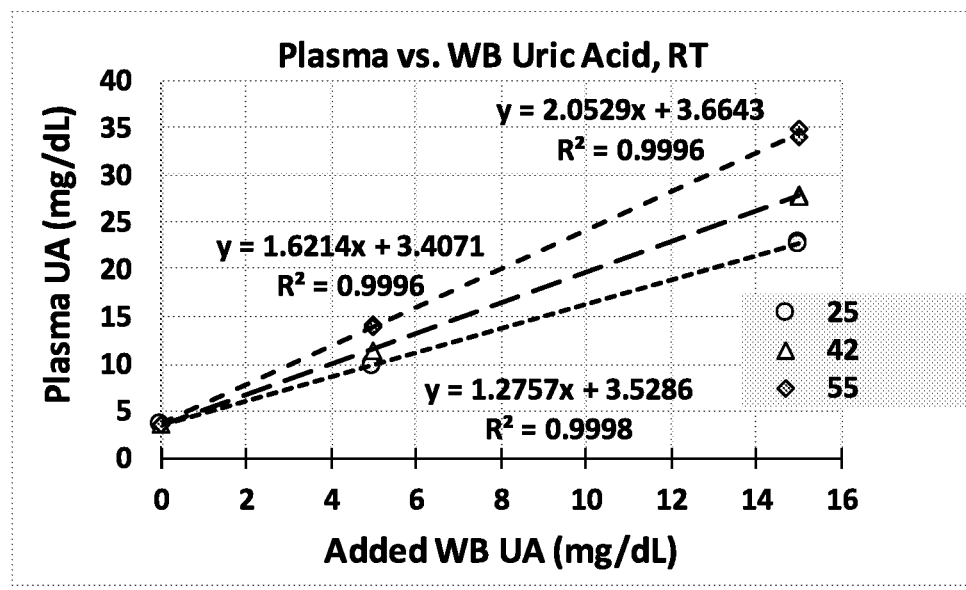
FIG. 10 illustrates correlations of plasma uric acid concentrations and added whole blood uric acid concentrations, in accord with aspects of the present disclosure.

Specifically, FIG. 8 shows the correlation plots for three current ratios $i_{G2-4}$, $i_{G3-4}$, and $i_{G4-4}$ with data from study 1. FIG. 9 shows the correlation plots for the current $i_{G3-4}$ from study 2 at three hematocrit levels. FIG. 10 shows the correlations of plasma uric acid concentrations and the added whole blood uric acid concentrations for the uric acid-Hct study. The direct currents $i_{G2-4}$, $i_{G3-4}$, and $i_{G4-4}$ were measured and shown to be correlated with the added uric acid concentration. Specifically, as shown in FIG. 8, currents $i_{G3-4}$ and $i_{G4-4}$ gave high correlations with the added uric acid concentrations with very similar sensitivity (correlation slope). Current $i_{G2-4}$ was much less sensitive compared to the other two and its correlation coefficient's $R^2$ value was not as strong due to only partial oxidation at 0.35 V. Further, due to oxidations of other likely species, the current $i_{G4-4}$ at 1.0 V gave a much higher intercept. On the other hand, the current $i_{G3-4}$ had the same sensitivity with a much lower intercept and, therefore, was more favorable as a representative signal for uric acid. All three currents may be used as risk factor parameters for uric acid.

Figure 11:
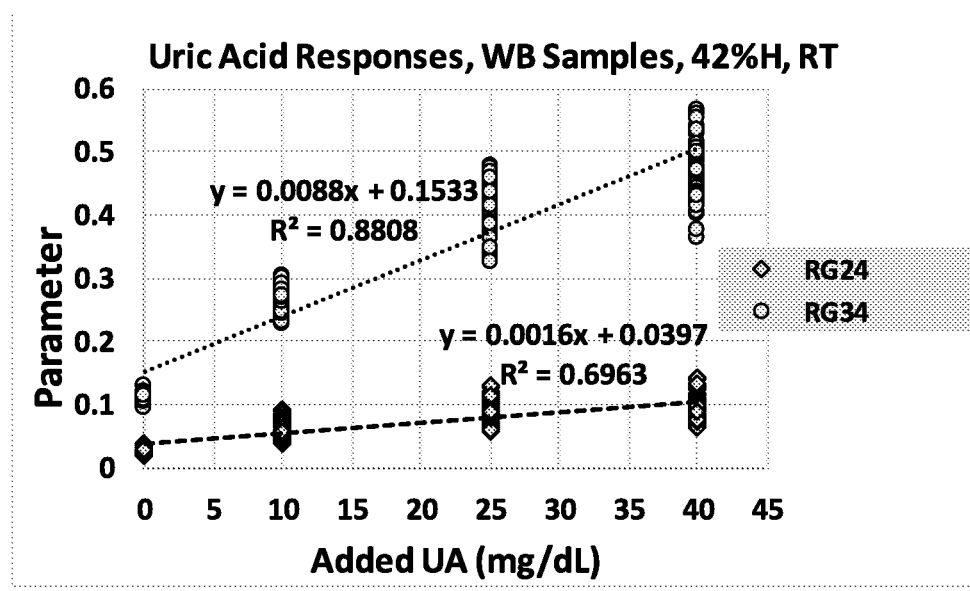
FIG. 11 illustrates correlation plots of the parameters $RG_{24}$ and $RG_{34}$ with the added uric acid concentrations from the same lab study as in FIG. 8, in accord with aspects of the present disclosure.
Figure 12:
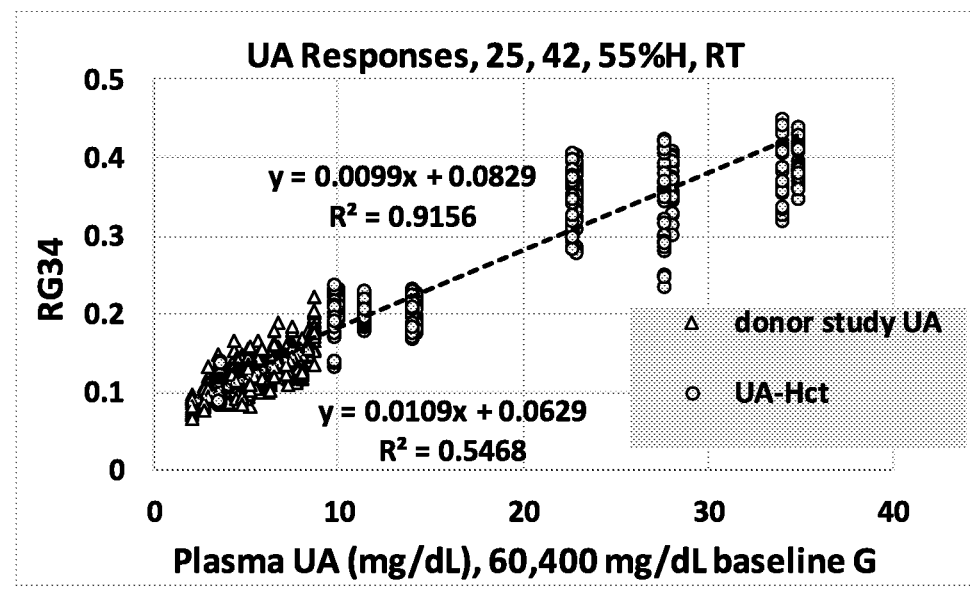
FIG. 12 illustrates correlation plots of the parameter $RG_{34}$ with plasma uric acid concentrations determined from samples of the same lab hematocrit study with uric acid and the same donor study in FIG. 9, in accord with aspects of the present disclosure.

Risk factor parameters computed from the inter-pulse ratio currents, such as $RG_{24}$ (i.e., $i_{G2-4}/i_{G4-4}$) and $RG_{34}$ (i.e., $i_{G3-4}/i_{G4-4}$), may also be used. FIG. 11 shows the correlation plots of the parameters $RG_{24}$ and $RG_{34}$ with the added uric acid concentrations from study 1 above, in accord with aspects of the present disclosure. FIG. 12 shows the correlation plots of the parameter $RG_{34}$ with the plasma uric acid concentrations determined from samples of a lab Hct study and a donor study, in accord with aspects of the present disclosure. Although $RG_{34}$ continues to be more sensitive than $RG_{24}$ relative to their counterpart of $i_{G2-4}$ and $i_{G3-4}$ as normalized by $i_{G4-4}$, $RG_{34}$ is shown to be less sensitive to hematocrit as compared to the direct current correlation in FIG. 9. Among the parameters including the G pulse currents, $RG_{34}$ had the highest $R^2$ value indicating its strongest correlation with the uric acid concentrations. FIG. 12 shows that the $RG_{34}$ parameter from whole blood samples of an internal donor study match the trend line obtained from a lab Hct study of uric acid with three hematocrit levels (25, 42, and 55%) and to baseline glucose (60 and 400 mg/dL).

Two studies were carried out that show the ability to determine risk factor parameters related to the concentration of triglyceride. Study 1 included baseline glucose concentrations of 80 and 240 mg/dL, added uric acid concentrations of 0 and 5 mg/dL, and added triglyceride concentrations of 0, 250, 500, 750, and 1000 mg/dL for each glucose/uric acid level, a hematocrit level of 42%, and a temperature of 22±2° C. (RT). Study 2 included baseline glucose concentrations of 80 and 300 mg/dL, added triglyceride concentrations of 0, 100, 200, 400, and 750 mg/dL for each baseline glucose concentration, a hematocrit level of 42%, and a study temperature of 22±2° C. (RT).

Figure 13:
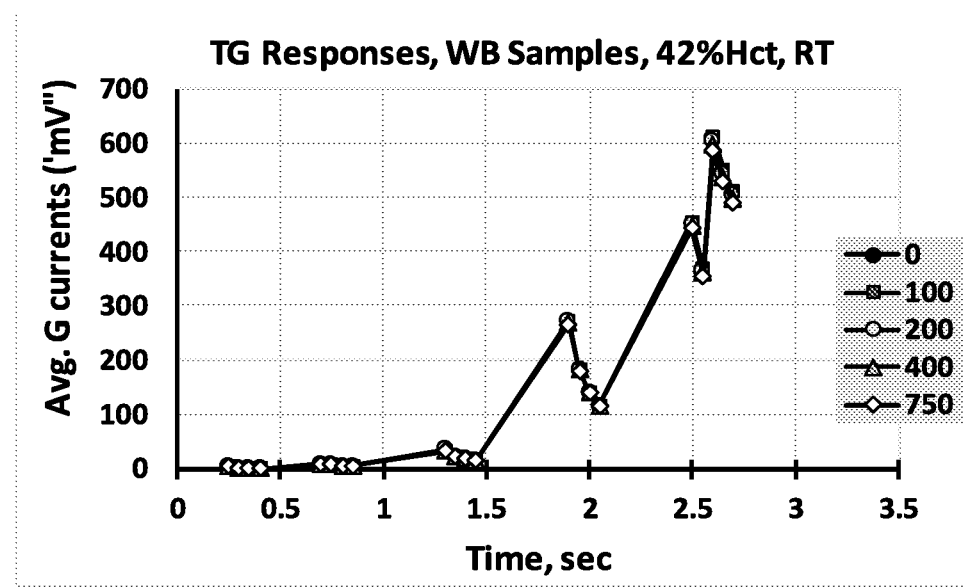
FIG. 13 is a graph illustrating average direct current profiles, according to the pulsing sequence in FIG. 3 with the G input signal, of blood samples containing four added levels of triglyceride that are used to determine one or more risk factor parameters, in accord with aspects of the present disclosure.
Figure 14:
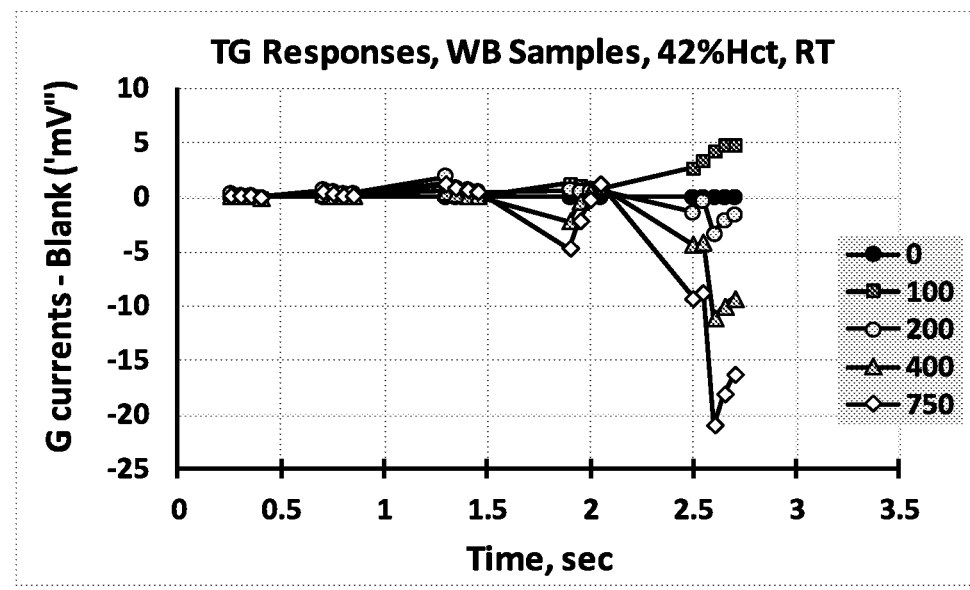
FIG. 14 is a graph illustrating normalized direct current profiles of blood samples from FIG. 13 containing triglyceride that are used to determine one or more risk factor parameters, in accord with aspects of the present disclosure.

Referring to FIG. 13, illustrated are the direct current profiles of the average G pulses for samples containing triglyceride at concentrations of 0, 250, 500, 750, and 1000 mg/dL in response to the input signal of FIG. 3. FIG. 14 illustrates the baseline correct current profiles in FIG. 13. As shown in FIG. 13, the response currents increase progressively with increasing applied voltages. However, as shown in FIG. 14, the profiles of the current differences do not show the increments in response to the added triglyceride amounts. Instead, subtle changes occur in the later G pulses (e.g., 1.0 V, 1.3 V, and 1.5 V). For instance, the decay behavior at G pulse 4 changes in response to the added triglyceride amounts relative to the baseline currents (no added triglyceride). Furthermore, the G pulses 5 and 6 each have some negative changes relative to the baseline currents. These behaviors are typical for large molecules, such as triglyceride and cholesterol, where no direct oxidation sites are readily available. Parameters describing pulsing decay were used to indicate triglyceride's presence.

Figure 15:
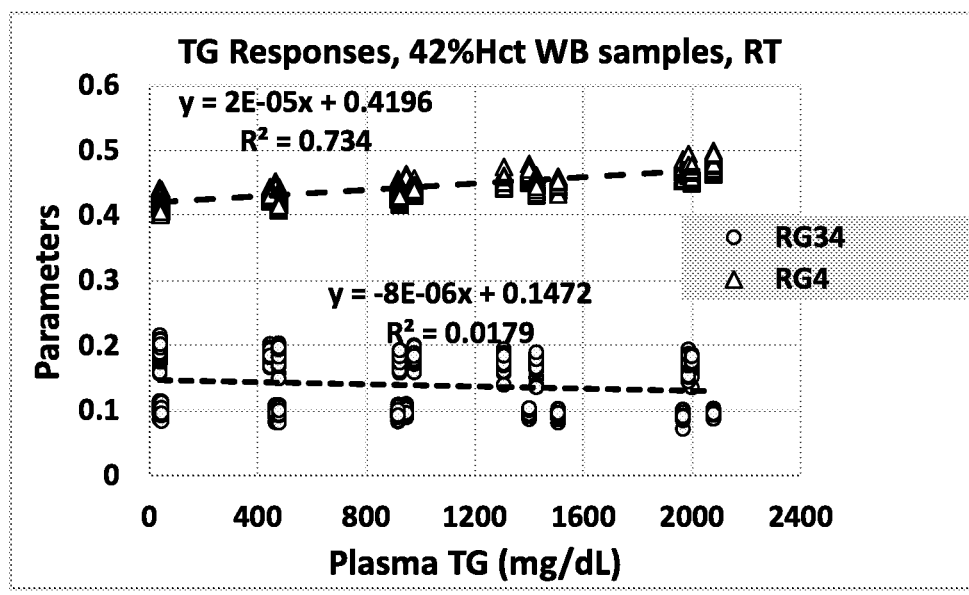
FIG. 15 illustrates a plot of $RG_4$ and $RG_{34}$ against the plasma triglyceride concentrations determined by Beckman instrument, in accord with aspects of the present disclosure.

Accordingly, intra- and inter-pulse ratios based on the later G pulses (e.g., 1.0 V, 1.3 V, and 1.5 V) can be used for generating risk factor parameters associated with triglyceride. The risk factor parameters can be generated from intra- or inter-pulse ratios based on the direct currents (FIG. 13) or baseline corrected currents (FIG. 14). Further, the risk factor parameters can vary between endogenous species. For example, one of such direct parameter was RG4 (i.e., $i_{G4-4}/i_{G4-1}$). FIG. 15 shows a plot of $RG_4$ and $RG_{34}$ (i.e., $i_{G3-4}/i_{G4-4}$) against the plasma triglyceride concentrations. It can be seen from this plot that the strong uric acid indicating parameter $RG_{34}$ was not responsive to triglyceride.

One study was carried out to show the ability to determine risk factor parameters related to the concentration of 3-hydroxybutyric acid. Compared to the uric acid and triglyceride which are present in the blood all the time at varying amounts with slow temporal changes over a period of time, 3-HBA only spikes high at the onset of ketoacidosis, which may be rare or none for many people with diabetes. Thus, the value of monitoring the risk factor parameters related to 3-HBA may be to provide a timely warning for potential life threatening events due to the abnormally high 3-HBA levels (>3 mmol). The study was conducted using baseline glucose concentrations of 80 and 300 mg/dL, added 3-hydroxybutyric acid concentrations of 0, 0.5, 0.98, 2.94, and 5.88 mmol for each baseline glucose concentration, a hematocrit level of 42%, and a temperature of 22±2° C. (RT).

Figure 16:
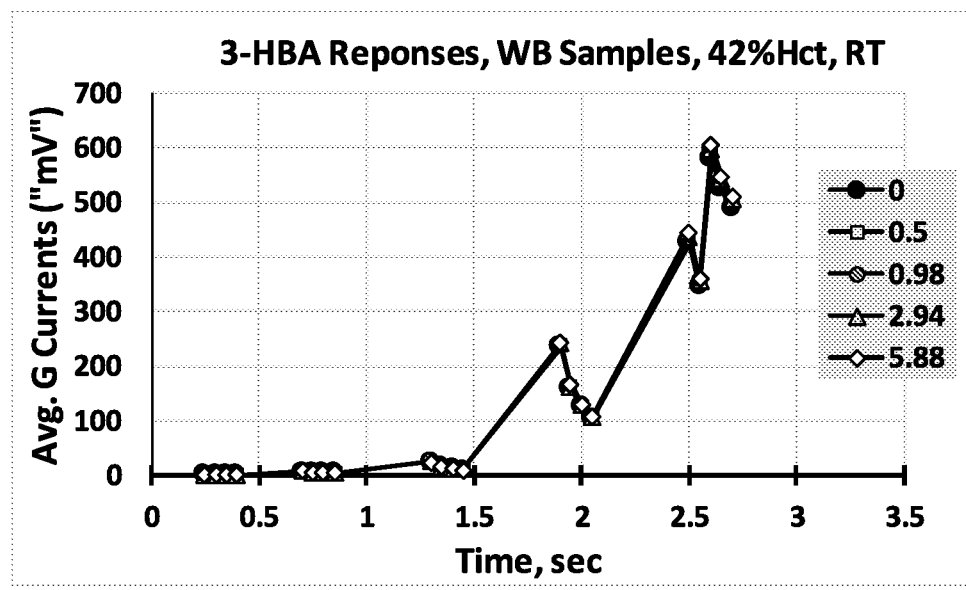
FIG. 16 is a graph illustrating average direct current profiles, according to the pulsing sequence in FIG. 3 with the G input signal, of blood samples containing four added levels of 3-hydroxybutyric acid that are used to determine one or more risk factor parameters, in accord with aspects of the present disclosure.
Figure 17:
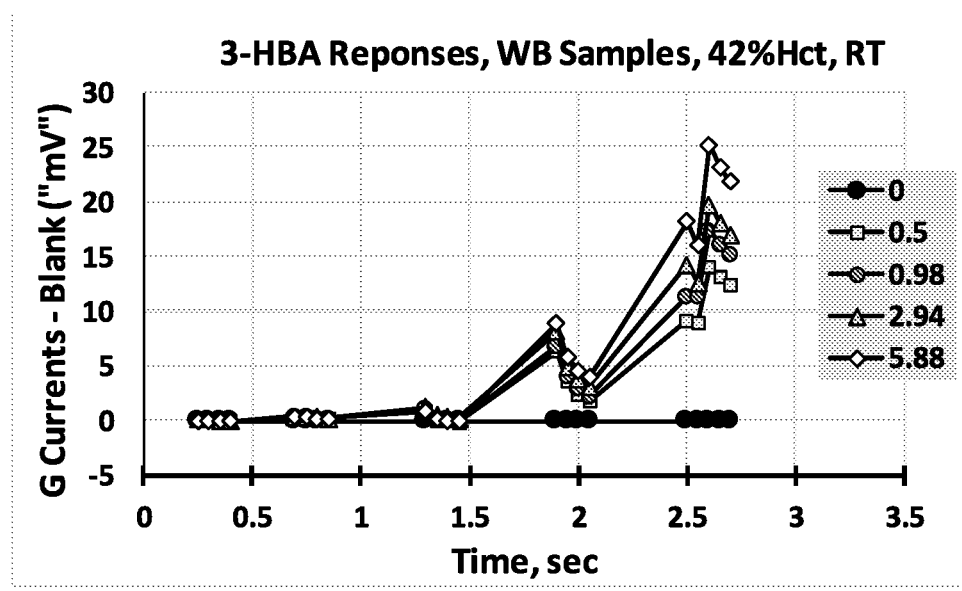
FIG. 17 is a graph illustrating normalized direct current profiles of blood samples from FIG. 16 containing 3-hydroxybutyric acid that are used to determine one or more risk factor parameters, in accord with aspects of the present disclosure.

Referring to FIG. 16, illustrated are the direct current profiles of the average G pulses for samples containing 3-hydroxybutyric acid at concentrations of 0, 0.5, 0.98, 2.94, and 5.88 mmol in response to the input signal of FIG. 3. As shown, the direct current profiles of the average G pulses show little change. FIG. 17 shows that, upon subtracting the baseline currents from currents with added 3-hydroxybutyric acid, positive oxidation currents are visible at higher voltage pulses (e.g., 1.3 V and 1.5 V).

The result was positive currents $i_{G6-3}$ in response to the additions of 3-HBA to the whole blood samples. While the positive currents may provide the indication of the presence of 3-HBA, taking the ratio of $i_{G6-3}/i_{G4-4}$ to make $RG_{64}$ reduced the lot-to-lot and sensor-to-sensor variability. Accordingly, intra- and inter-pulse ratios based on the G pulses at 1.3 V and 1.5 V can be used for generating risk factor parameters associated with 3-hydroxybutyric acid based on the G pulse at 1.3 V and 1.5 V being responsive to the concentration of 3-hydroxybutyric acid in the sample. Further risk factor parameters can be generated from intra- or inter-pulse ratios based on the direct currents (FIG. 16) or baseline corrected currents (FIG. 17).

Figure 18:
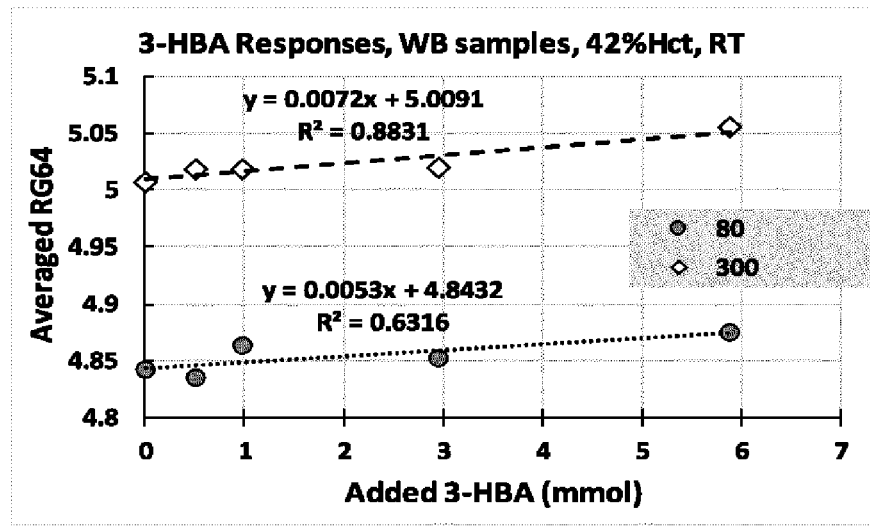
FIG. 18 illustrates the $RG_{64}$ response curves of 3-hydroxybutyric acid at two baseline glucose concentrations, in accord with aspects of the present disclosure.
Figure 19:
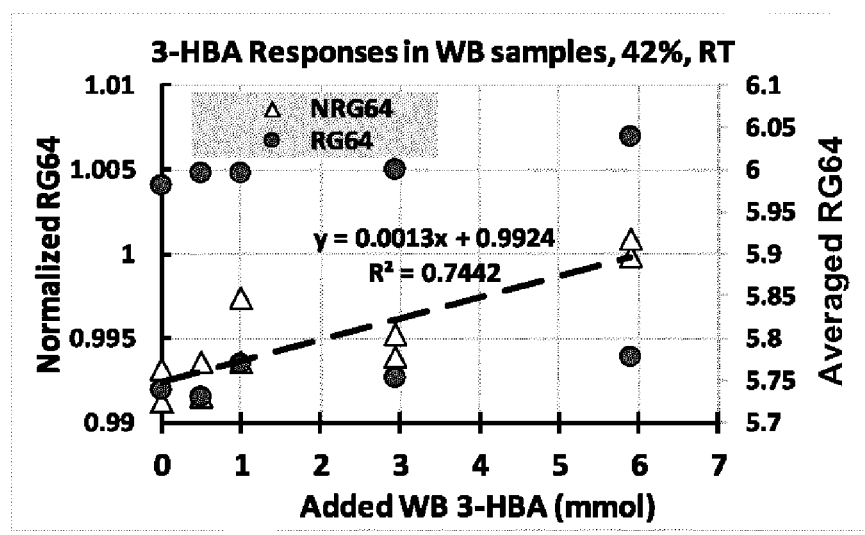
FIG. 19 illustrates $RG_{64}$ and normalized $RG_{64}$ values versus added 3-HBA, in accord with aspects of the present disclosure.
Figure 20:
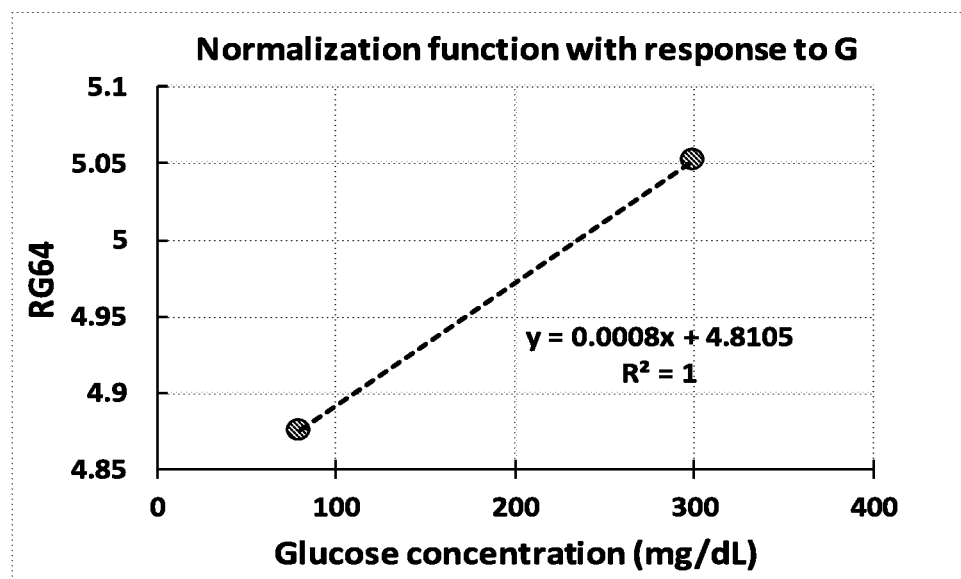
FIG. 20 illustrates the normalizing function where the glucose dependence of $RG_{64}$ response with respect to 3-hydroxybutyric acid is to be removed, in accord with aspects of the present disclosure.

FIG. 18 illustrates the response curves/lines at two baseline glucose concentrations, in accord with aspects of the present disclosure, both of which gave a good correlation between the parameter $RG_{64}$ and the added 3-hydroxybutyric acid concentrations. FIG. 19 illustrates a normalized $RG_{64}$ value ($NRG_{64}$) versus added 3-hydroxybutyric acid in comparison to the direct $RG_{64}$ parameter, in accord with aspects of the present disclosure. The $NRG_{64}$ parameter substantially removed the glucose dependence for the $RG_{64}$ parameter. The glucose concentration for normalization of the dependence of the $RG_{64}$ on glucose in real-time detection may be substituted with the BGM glucose reading. FIG. 20 illustrates the normalization function for the glucose dependence of the $RG_{64}$ response curves/lines for 3-HBA. Such normalization can be that as disclosed in U.S. patent application Ser. No. 14/774,617, which is incorporated by reference herein in its entirety.

Thus, using the various risk factor parameters of the associated endogenous species within a sample, information can be extracted from the sample that is otherwise lost using conventional biosensor systems. The information can be used to generate a patient profile that shows analyte concentrations, such as glucose concentrations, over a period of time, in addition to one or more risk factor parameters over the period of time. The risk factor parameters provide additional information on risk factors associated with the user from which the samples were withdrawn. The additional information can be used by the user or a medical professional to monitor the user's health, diagnose certain medical conditions, determine risks for developing certain medical conditions, among others use.

Figure 21:
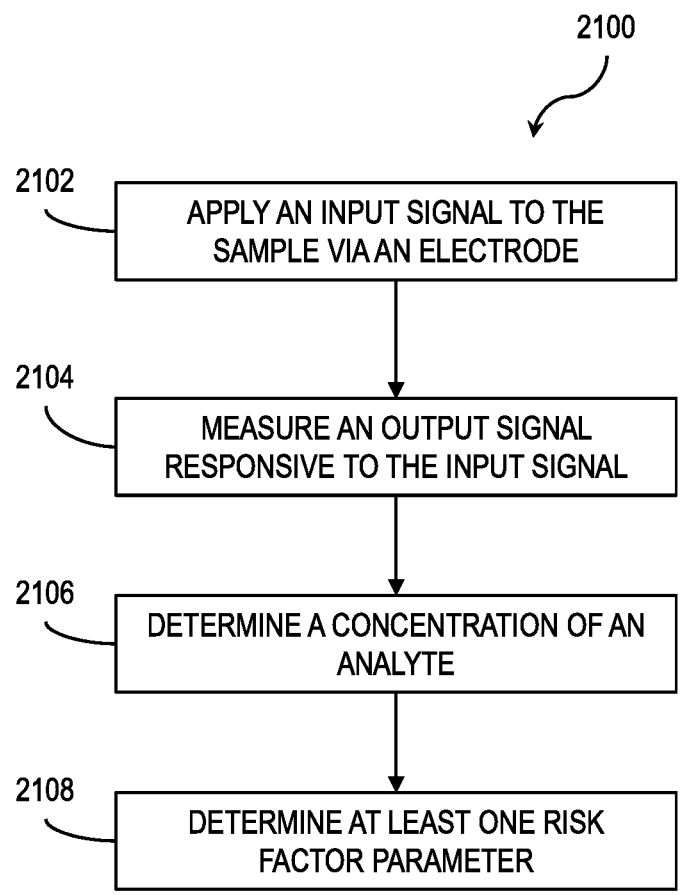
FIG. 21 is a flowchart of a process for electrochemically analyzing a sample, in accord with aspects of the present disclosure.

FIG. 21 is a flowchart of a process 2100 for electrochemically analyzing a sample and, in particular, determining a risk factor parameter during the analysis, in accord with aspects of the present disclosure. The process 2100 can be performed by a biosensor system, such as the biosensor system 100 discussed above. In specific aspects, the biosensor system performing the process 2100 can be a device for determining the concentration of glucose in a blood sample such as a blood glucose monitoring device, a continuous glucose monitor, and the like.

At step 2102, an input signal is applied to a sample via an electrode according to the above concepts, in which the input signal has at least one excitation. As discussed above, the sample can be whole blood. However, the sample can be any other biological sample.

The at least one excitation can be amperometric excitation or a voltammetric excitation. In some embodiments, the input signal can be applied to the sample via an electrode having a reagent. For example, the electrode can include a reagent that facilitates oxidation of an analyte in the sample, at least one other species in the sample, or a combination thereof. In some embodiments, the input signal can be applied to the sample via an electrode lacking a reagent. For example, the electrode can exclude any reagent that facilitates oxidation of any species in the sample.

In some embodiments, the input signal can be applied to the sample via both an electrode having a reagent and an electrode lacking a reagent, such as when the input signal has an input signal portion applied via the electrode having a reagent and an input signal portion applied via the electrode lacking the reagent, or when the input signal is comprised of multiple signals. For example, in some embodiments, the input signal can be a first input signal, applied via a first electrode having a reagent, intertwined with a second input signal, applied via a second electrode lacking a reagent. The intertwining can include applying to the sample, via the first electrode, the first input signal having at least one excitation and a relaxation, and applying to the sample, via the second electrode, the second input signal having at least one excitation and a relaxation, such that the at least one excitation of the first input signal is nonconcurrent with the at least one excitation of the second input signal.

In some embodiments, the potential of the at least one excitation can be selected so as to correspond to an amount of the at least one species in the sample. In some embodiments, the potential of the at least one excitation can be selected based on an oxidation potential of the at least one species, a decay rate of current measurements in response to the at least one excitation, or a combination thereof.

At step 2104, an output signal responsive to the input signal is measured. In some embodiments, the output signal can be responsive to the concentration of the analyte in the sample, such as when at least a portion of the input signal is applied via an electrode with a reagent specific to the analyte. In some embodiments, the output signal is not responsive to the concentration of the analyte in the sample, such as when no portion of the input signal is applied via an electrode with a reagent specific to the analyte. Further, for the at least one excitation of the input signal, one or more currents can be measured in generating the output signal. For example, one, two, three, four, five, six, seven, eight, nine, ten, or more output currents can be measured in response to the at least one excitation of the input signal.

At step 2106, a concentration of an analyte within the sample is determined based on the output signal. The concentration can be determined according to various techniques known in the art. For example, the output signal can be analyzed according to one or more reference correlations, one or more error compensations, and/or one or more error detections for determining the concentration of the analyte based on the output signal.

At step 2108, at least one risk factor parameter associated with at least one species in the sample, other than the analyte, is determined in accord with the aspects disclosed above. The at least one species is an endogenous species found within the sample, and a species other than the analyte. For example, the endogenous species can be uric acid, cholesterol, triglyceride, acetaminophen, ascorbic acid, bilirubin, dopamine, hemoglobin, xylose, and/or 3-hydroxybutyric acid, or other species that can be found in a sample, such as a blood sample.

Where the potential of the at least one excitation discussed above is selected according to the endogenous species, the at least one excitation can have a constant potential of about 0.35 V to about 0.5 V when the at least one species is uric acid. The at least one excitation alternatively can have a constant potential of about 1 V to about 1.5 V where the at least one species is triglyceride. The at least one excitation alternatively can have a constant potential of about 1.3 V to about 1.5 V where the at least one species is 3-hydroxybutyric acid.

In embodiments where the output signal includes a plurality of current measurements responsive to the at least one excitation, the determination of the at least one risk factor parameter can be based on at least one current measurement of the plurality of current measurements, a ratio of two current measurements of the plurality of current measurements, or a combination thereof. In some specific embodiments, the two current measurements can be a last current measurement of the plurality of current measurements and a first current measurement of the plurality of current measurements. For example, the two current measurements can be in response to a same excitation of the at least one excitation. Alternatively, the two current measurements can be in response to two different excitations of the at least one excitation.

In some embodiments, the process 2100 can further include repeating the steps 2102 through 2108 for multiple separate samples over time, and further can include logging the analyte concentration and the at least one risk factor parameter for the multiple samples within a patient profile. From the patient profile, one or more trends can be determined in the log of the at least one risk factor parameter, and the trends can indicate a progression of a medical condition associated with the at least one species. In some embodiments, the biosensor system can provide an indication that at least one risk factor parameter satisfies a threshold. The threshold can be associated with a progression of the medical condition. For example, the threshold can be associated a progression, an indication, or a combination thereof of a medical condition, such that satisfying or not satisfying the threshold indicates the progression, indication, or a combination thereof of the medical condition. For example, the biosensor system can provide warning to the user if a risk factor parameter become outside a set limits. As applied to 3-HBA, such limits can be for when levels of 3-HBA in whole blood are greater than 1 mmol/L require attention, and the attention can be reporting the same to a doctor, or such limits can be for when levels of 3-HBA are greater than 3 mmol/L, and the attention can be seeking immediate medical attention (e.g., visiting the emergency room).

Based on the foregoing, and as applied to diabetes as an example, a biosensor system for monitoring glucose having a function of whole blood profiling, which includes determination of the glucose concentration and one or more risk factor parameters, will enhance the diabetes care management. Specifically, the biosensor system can store the whole blood profile in terms of the risk factor parameters along with the whole blood glucose readings. Thus, reporting the determined concentration of endogenous species, such as, for example, %-Hct, uric acid, and cholesterol, or one or more of their risk factor parameters, along with the determined glucose concentration, provides a long term whole blood profile of a user, reflecting the progressive change, or lack thereof over time, thus benefiting the diabetes care/management. As an example, the recorded/logged determined parameters may be: glucose, %-Hct (as simply by the $i_{H-4}$ current), $i_{G2-4}$, $i_{G3-4}$, $i_{G4-4}$, $i_{G5-2}$, $i_{G6-3}$, $RG_{34}$, $RG_4$, $NRG_{64}$. In another example, the recorded/logged parameters may be: glucose, %-Hct (as simply by the $i_{H-4}$ current), $i_{G3-4}$, $i_{G4-4}$, $i_{G5-2}$, $i_{G6-3}$, $RG_{34}$, $RG_4$, $NRG_{64}$, $RG_{56}$ ($i_{5-2}/i_{G6-3}$), $RHG_4$ ($i_{H-4}/i_{G4-4}$).

While various embodiments of the invention have been described, it will be apparent to those of ordinary skill in the art that other embodiments and implementations are possible within the scope of the invention.

Each of these embodiments, and obvious variations thereof, is contemplated as falling within the spirit and scope of the claimed invention(s), which are set forth in the following claims. Moreover, the present concepts expressly include any and all combinations and sub-combinations of the preceding elements and aspects.

What is claimed is:

1. A method of electrochemically analyzing a sample comprising:
    applying an input signal, via an electrode, to the sample, the input signal having at least one excitation;
    measuring an output signal responsive to the input signal;
    determining a concentration of an analyte within the sample based on the output signal; and
    determining at least one risk factor parameter associated with at least one species in the sample other than the analyte based on one or more of intra-pulse ratios, one or more inter-pulse ratios, or a combination thereof of current measurements within the output signal.

2. The method of claim 1, wherein a potential of the at least one excitation is selected so as to correspond to an amount of the at least one species in the sample.

3. The method of claim 1, wherein a potential of the at least one excitation is selected based on an oxidation potential of the at least one species, a decay rate of current measurements in response to the at least one excitation, or a combination thereof.

4. The method of claim 1, wherein the output signal includes a plurality of current measurements responsive to the at least one excitation, and the determination of the at least one risk factor parameter is based on at least one current measurement of the plurality of current measurements, a ratio of two current measurements of the plurality of current measurements, or a combination thereof.

5. The method of claim 4, wherein the two current measurements are a last current measurement of the plurality of current measurements and a first current measurement of the plurality of current measurements.

6. The method of claim 5, wherein the two current measurements are in response to a same excitation of the at least one excitation.

7. The method of claim 5, wherein the two current measurements are in response to two different excitations of the at least one excitation.

8. The method of claim 1, further comprising:
    repeating the steps of the applying, the measuring, the determining of the concentration, and the determining of the at least one risk factor parameter for multiple separate samples over time; and
    logging the analyte concentration and the at least one risk factor parameter for the multiple samples within a patient profile.

9. The method of claim 8, further comprising:
    determining at least one trend in the log of the at least one risk factor parameter, wherein the at least one trend indicates a progression of a medical condition associated with the at least one species.

10. The method of claim 9, further comprising:
providing an indication that at least one risk factor parameter satisfies a threshold,
wherein the threshold is associated with a progression of the medical condition.

11. The method of claim 1, wherein the at least one species is an endogenous species.

12. The method of claim 11, wherein the endogenous species is one or more of uric acid, cholesterol, triglyceride, acetaminophen, ascorbic acid, bilirubin, dopamine, hemoglobin, xylose, and 3-hydroxybutyric acid.

13. The method of claim 1, wherein the electrode excludes any reagent that facilitates oxidation of the analyte, the at least one species, or a combination thereof.

14. The method of claim 1, wherein the electrode includes a reagent that facilitates oxidation of the analyte, the at least one species, or a combination thereof.

15. The method of claim 1, wherein the at least one excitation has a constant potential of about 0.35 V to about 0.5 V, and the at least one species is uric acid.

16. The method of claim 1, wherein the at least one excitation has a constant potential of about 1 V to about 1.5 V, and the at least one species is triglyceride.

17. The method of claim 1, wherein the at least one excitation has a constant potential of about 1.3 V to about 1.5 V, and the at least one species is 3-hydroxybutyric acid.

18. The method of claim 1, wherein the at least one excitation is an amperometric excitation.

19. The method of claim 1, wherein the at least one excitation is a voltammetric excitation.

20. The method of claim 1, wherein the output signal is responsive to the concentration of the analyte in the sample.

21. The method of claim 1, wherein the output signal is not responsive to the concentration of the analyte in the sample.

22. A method of generating a patient profile comprising:
intertwining a first input signal, via a first electrode having a reagent, with a second input signal, via a second electrode lacking a reagent, the intertwining including:
applying to the sample, via the first electrode, the first input signal having at least one excitation and a relaxation, and applying to the sample, via the second electrode, the second input signal having at least one excitation and a relaxation, such that the at least one excitation of the first input signal is nonconcurrent with the at least one excitation of the second input signal;
measuring a first output signal responsive to the first input signal and a second output signal responsive to the second input signal;
determining the concentration of the analyte based on at least the first output signal and the second output signal; and
determining at least one risk factor parameter associated with at least one endogenous species in the sample based on at least the second output signal.

23. The method of claim 22, wherein the second output signal includes at least one response for the at least one excitation, and the determining of the at least one risk factor parameter is based on the at least one response.

24. The method of claim 22, wherein the second output signal includes at least two responses for the at least one excitation, and the determining of the at least one risk factor parameter is based on the at least two responses.

25. The method of claim 22, wherein the second output signal includes at least one response for a first excitation of the at least one excitation and at least one response for a second excitation of the at least one excitation, and the determining of the at least one risk factor parameter is based on the at least two responses.

26. The method of claim 22, wherein the first output signal is responsive to the concentration of the analyte in the sample.

27. The method of claim 26, wherein the second output signal is not responsive to the concentration of the analyte in the sample.

28. The method of claim 22, wherein the first output signal is responsive to a redox reaction of the analyte.

29. The method of claim 28, wherein the second out signal is not responsive to the redox reaction of the analyte.

30. The method of claim 22, wherein the analyte is glucose, and the endogenous species is one or more of uric acid, cholesterol, triglyceride, acetaminophen, ascorbic acid, bilirubin, dopamine, hemoglobin, xylose, and 3-hydroxybutyric acid.

31. The method of claim 22, wherein the determining the at least one risk factor parameter associated with the at least one endogenous species in the sample is based on (i) one or more intra-pulse ratios of current measurements within the first output signal, the second output signal, or a combination thereof, or (2) one or more intertwined pulse ratios of current measurements within the first and second output signals.

32. A method of analyzing a sample with a blood glucose monitoring device, the method comprising:
applying an input signal to the sample via a bare electrode of the blood glucose monitoring device, the input signal including a constant voltage pulse;
determining at least one risk factor parameter associated with at least one endogenous species in the sample in response to the constant voltage pulse; and
logging the at least one risk factor parameter within a patient profile stored in the blood glucose monitoring device.

33. The method of claim 32, further comprising:
repeating the steps of the applying, the determining, and the logging for multiple separate samples over time;
determining at least one trend in the log of the at least one risk factor parameter; and
providing an indication that at least one logged value for the at least one risk factor parameter satisfies a threshold associated with a progression, an indication, or a combination thereof of the medical condition.

34. The method of claim 32, wherein the constant voltage pulse has a potential of about 0.35 V to about 0.5 V, and the at least one species is uric acid.

35. The method of claim 32, wherein the constant voltage pulse has a potential of about 1 V to about 1.5 V, and the at least one species is triglyceride.

36. The method of claim 32, wherein the constant voltage pulse has a potential of about 1.3 V to about 1.5 V, and the at least one species is 3-hydroxybutyric acid.

* * * * *